(12) United States Patent
Facchetti et al.

(10) Patent No.: US 9,932,362 B2
(45) Date of Patent: Apr. 3, 2018

(54) PROCESSES FOR THE PREPARATION OF RUTHENIUM OR OSMIUM COMPLEXES COMPRISING P AND N DONOR LIGANDS

(71) Applicant: JOHNSON MATTHEY PUBLIC LIMITED COMPANY, London (GB)

(72) Inventors: Sarah Facchetti, Cambridge (GB); Hans Nedden, Cambridge (GB)

(73) Assignee: Johnson Matthey Public Limited Company, London, England (GB)

(*) Notice: Subject to any disclaimer, the term of this patent is extended or adjusted under 35 U.S.C. 154(b) by 0 days.

(21) Appl. No.: 15/039,295

(22) PCT Filed: Nov. 25, 2014

(86) PCT No.: PCT/GB2014/053465
§ 371 (c)(1),
(2) Date: May 25, 2016

(87) PCT Pub. No.: WO2015/079207
PCT Pub. Date: Jun. 4, 2015

(65) Prior Publication Data
US 2017/0081350 A1 Mar. 23, 2017

(30) Foreign Application Priority Data
Nov. 26, 2013 (GB) .................... 1320869.9

(51) Int. Cl.
C07F 15/00 (2006.01)
C07F 9/28 (2006.01)
C07F 17/02 (2006.01)

(52) U.S. Cl.
CPC .......... *C07F 15/0053* (2013.01); *C07F 17/02* (2013.01)

(58) Field of Classification Search
CPC .................................... C07F 15/00
USPC ....................................... 546/2, 22
See application file for complete search history.

(56) References Cited

FOREIGN PATENT DOCUMENTS

| EP | 2789623 | 10/2014 | | |
|---|---|---|---|---|
| WO | 2005105819 | 11/2005 | | |
| WO | 2009149670 | 12/2009 | | |
| WO | WO 2014/166777 A1 * | 10/2014 | ............. | C07F 15/00 |

OTHER PUBLICATIONS

Malecki, J.G.: Synthesis, crystal, molecular and electronic structures of thiocyanate ruthenium complexes with pyridine and its derivatives as ligands. Plyhedron, vol. 29, pp. 1973-1979, 2010.*
Gomez Arrayas et al.: "Recent applications of chiral ferrocene ligands in asymmetric catalysis", Angewandte Chemie International Edition, Wiley-VCH Verlag GmbH & Co., vol. 45, No. 46, Nov. 27, 2006, pp. 7674-7715, XP009098057.
Baratta et al.: "Osmium pyme complexes for fast hydrogenation and asymmetric transfer hydrogenation of ketones", Chemistry—A European Journal, Wiley-VCH Verlag GmbH & Co. KGaA, Weinheim, DE, vol. 14, No. 8, Mar. 7, 2008, pp. 2557-2563, XP002571494.
Baratta et al.: "Pincer and Diamine Ru and Os Diphosphane Complexes as Efficient Catalysts for the Dehydrogenation of Alcohols to Ketones", Chemistry—A European Journal, vol. 17, No. 12, Feb. 21, 2011, pp. 3474-3481, XP55009415.
Del Zotto et al., : "Transfer Hydrogenation Reactions Catalyzed by Free or Silica-Immobilized [RuC12(ampy){RN(CH2PPh2)2}] Complexes", European Journal of Inorganic Chemistry, vol. 2007, No. 18, Jun. 1, 2007, pp. 2909-2916, XP055163294.
Baratta et al.: "2-(Aminomethyl)pyridine-Phosphine Ruthenium (II) Complexes: Novel Highly Active Transfer Hydrogenation Catalysts", Organometallics, 2005, vol. 24, No. 7, pp. 1660-1669, XP001236745.

* cited by examiner

*Primary Examiner* — Charanjit Aulakh
(74) *Attorney, Agent, or Firm* — Baker & Hostetler LLP

(57) ABSTRACT

An improved processes for the preparation of ruthenium or osmium complexes including P and N donor ligands, in particular, ruthenium complexes.

14 Claims, No Drawings

PROCESSES FOR THE PREPARATION OF RUTHENIUM OR OSMIUM COMPLEXES COMPRISING P AND N DONOR LIGANDS

The present invention relates to improved processes for the preparation of ruthenium or osmium complexes comprising P and N donor ligands, in particular, ruthenium complexes.

Jung et al (Inorganic Chemistry, 1984, 23, 726-729) describes the reactions of $Ph_2P(CH_2)_nPPh_2$ (n=1-4) with $RuCl_2(PPh_3)_3$. The process described in Jung et al for the preparation of $RuCl_2(PPh_3)(Ph_2P(CH_2)_4PPh_2)$, however, is not suitable for larger-scale manufacture as large volumes of solvents are needed to both carry out the reaction and to isolate the $RuCl_2(PPh_3)(Ph_2P(CH_2)_4PPh_2)$ complex. For example, the present inventors have found that 0.5 L of dichloromethane and 2.5 L of ethanol are needed for the conversion of 10 g of the Ru precursor $RuCl_2(PPh_3)_3$.

Baratta et al (Organometallics, 2005, 24, 1660-1669) describes the synthesis of 2-(aminomethyl)pyridine-phosphine ruthenium(II) complexes. The complexes represent an active class of catalysts in transfer hydrogenations and in hydrogenation reactions. The procedure described in Baratta et al for the synthesis of trans-$RuC_2$(dppb)(AMPY) is summarised below:

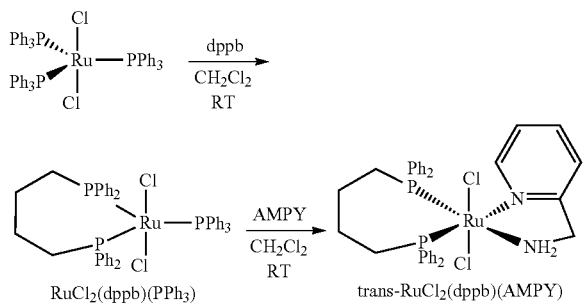

Synthesis of trans-$RuCl_2$(dppb)(AMPY)

dppb=1,4-bis(diphenylphosphino)butane; $CH_2Cl_2$=dichloromethane; RT=room temperature; AMPY=2-(aminomethyl)pyridine While the process described in Baratta et al may be used to prepare gram scale quantities of 2-(aminomethyl)pyridine-phosphine ruthenium(II) complexes, the process is not suitable for large scale manufacture. In this regard, the first step prepares $RuCl_2$(dppb)(PPh$_3$) as described in Jung et al and, as such, involves large volumes of solvent. The second step which synthesises trans-$RuCl_2$(dppb)(AMPY) has proven challenging on a larger scale in that it is difficult to separate the trans-$RuC_2$(dppb)(AMPY) from PPh$_3$. This is because, upon addition of heptane to the dichloromethane solution to precipitate the complex, the co-precipitation of the free phosphine occurs and only a small portion of trans-$RuC_2$(dppb)(AMPY) can be collected free of PPh$_3$ impurities.

Baratta et al (Organometallics, 2012, 31, 1133-1142) describes reactions involving carbonyl compounds and alcohols with the complexes [$MCl_2$(dppf)(ampy)] [M=Ru (cis-$RuCl_2$(dppf)(ampy)); M =Os (trans-$OsCl_2$(dppf)(ampy)); dppf=1,1'-bis(diphenylphosphino)ferrocene; ampy=2-aminomethylpyridine].

The present inventors have developed processes for the preparation of ruthenium complexes comprising P and N donor ligands which overcome problems associated with the prior art. The processes are more suited to large-scale manufacture of the ruthenium complexes.

SUMMARY OF THE INVENTION

In one aspect, the invention provides a process for the preparation of an [$M(X)_2(L^1)_m(L^2)$] complex, the process comprising the step of:
reacting an [$M(X)_2(L)_3$] complex with a phosphorus ligand $L^1$ and a bidentate N,N ligand $L^2$ in a ketone solvent to form the [$M(X)_2(L^1)_m(L^2)$] complex;
wherein,
M is ruthenium or osmium;
X is an anionic ligand;
L is a monodentate phosphorus ligand;
$L^1$ is a monodentate phosphorus ligand which is different to L, or a bidentate phosphorus ligand;
m is 1 or 2, wherein,
when m is 1, $L^1$ is a bidentate phosphorus ligand;
when m is 2, each $L^1$ is a monodentate phosphorus ligand; and
$L^2$ is a bidentate N,N ligand comprising a nitrogen-containing heteroaryl group and an amino group.

In another aspect, the invention provides a process for the preparation of an [$M(X)_2(L)_2(L^2)$] complex, the process comprising the step of:
reacting an [$M(X)_2(L)_3$] complex with a bidentate N,N ligand $L^2$ in a ketone solvent to form the [$M(X)_2(L)_2(L^2)$] complex;
wherein,
M is ruthenium or osmium;
X is an anionic ligand;
L is a monodentate phosphorus ligand; and
$L^2$ is a bidentate N,N ligand comprising a nitrogen-containing heteroaryl group and an amino group.

In yet another aspect, the invention provides a process for preparing an [$M(X)_2L(L^1)_m$] complex, the process comprising the step of:
reacting an [$M(X)_2(L)_3$] complex with a phosphorus ligand $L^1$ in a ketone solvent to form the [$M(X)_2L(L_1)_m$] complex;
wherein,
M is ruthenium or osmium;
X is an anionic ligand;
L is a monodentate phosphorus ligand;
$L^1$ is a monodentate phosphorus ligand which is different to L, or a bidentate phosphorus ligand;
m is 1 or 2, wherein,
when m is 1, $L^1$ is a bidentate phosphorus ligand; and
when m is 2, each $L^1$ is a monodentate phosphorus ligand.

In another aspect, the present invention provides a process for preparing a cis-[$M(X)_2(L^1)_m(L^2)$] complex, the process comprising the steps of:
a) treating a trans-[$M(X)_2(L^1)_m(L^2)$] complex in an alcohol solvent, an aromatic solvent or a mixture thereof; and
b) heating the reaction mixture to form the cis-[$M(X)_2(L)_m(L^2)$] complex;
wherein,
M is ruthenium or osmium;
X is an anionic ligand;
$L^1$ is a monodentate phosphorus ligand or a bidentate phosphorus ligand;
m is 1 or 2, wherein, when m is 1, $L^1$ is a bidentate phosphorus ligand;
when m is 2, each $L^1$ is a monodentate phosphorus ligand; and
$L^2$ is a bidentate N,N ligand comprising a nitrogen-containing heteroaryl group and an amino group.

In yet another aspect, the present invention provides a process for the preparation of a cis-$[M(X)_2(L^1)_m(L^2)]$ complex, the process comprising the step of:

reacting an $[M(X)_2(L)_2(L^2)]$ complex with a phosphorus ligand $L^1$ in an alcohol solvent, an aromatic solvent or a mixture thereof to form the cis-$[M(X)_2(L^1)_m(L^2)]$ complex;

wherein,
M is ruthenium or osmium;
X is an anionic ligand;
L is a monodentate phosphorus ligand;
$L^1$ is a monodentate phosphorus ligand which is different to L, or a bidentate phosphorus ligand;
m is 1 or 2, wherein,
when m is 1, $L^1$ is a bidentate phosphorus ligand;
when m is 2, each $L^1$ is a monodentate phosphorus ligand; and
$L^2$ is a bidentate N,N ligand comprising a nitrogen-containing heteroaryl group and an amino group.

In another aspect, the present invention provides a $[M(X)_2(L^1)(L^2)]$ complex, wherein:
M is ruthenium or osmium;
X is an anionic ligand;
$L^1$ is a bidentate phosphorus ligand selected from the group consisting of:
(i) a ligand of formula (Ia) or (Ib):

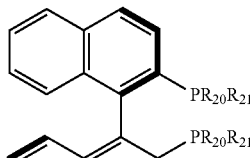
(Ia)

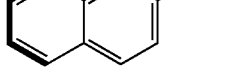
(Ib)

wherein,
$R_{20}$ and $R_{21}$ are each independently selected from the group consisting of unsubstituted $C_{3-20}$-cycloalkyl, substituted $C_{3-20}$-cycloalkyl, unsubstituted $C_{5-20}$-aryl and substituted $C_{5-20}$-aryl;

(ii) a ligand of formula (IIa) or (IIb):

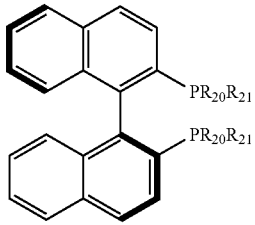
(IIa)

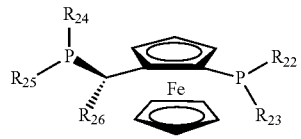
(IIb)

wherein,
$R_{22}$ and $R_{23}$ are independently selected from the group consisting of unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl;

$R_{24}$ and $R_{25}$ are independently selected from the group consisting of unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl; and $R_{26}$ is selected from the group consisting of unsubstituted $C_{1-20}$-alkyl and substituted $C_{1-20}$-alkyl;

(iii) a ligand of selected from the group consisting of 1,1'-bis(di-isopropylphosphino)ferrocene, 1,1'-bis(dicyclohexylphosphino)ferrocene and 1,1'-bis(di-tert-butylphosphino)ferrocene.

and
$L^2$ is a bidentate N,N ligand selected from the group consisting of ligands (1), (2) and (3):

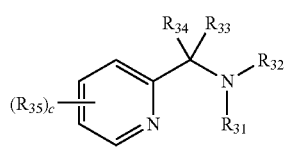
(1)

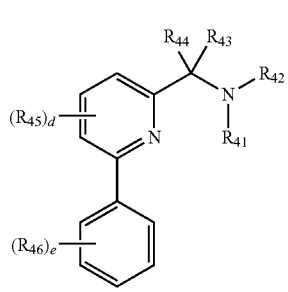
(2)

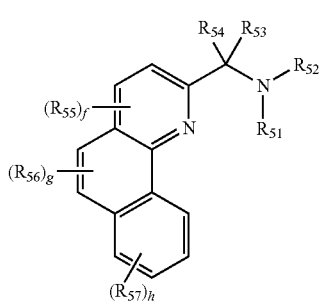

(3)

wherein:
- $R_{31}$ and $R_{32}$, $R_{41}$ and $R_{42}$, and $R_{51}$ and $R_{52}$ are independently selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl;
- $R_{33}$ and $R_{34}$, $R_{43}$ and $R_{44}$, and $R_{53}$ and $R_{54}$ are independently selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl;
- $R_{35}$, $R_{45}$, $R_{46}$, $R_{55}$, $R_{56}$ and $R_{57}$ are independently selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl;
- c is 0, 1, 2, 3 or 4;
- d is 0, 1, 2 or 3;
- e is 0, 1, 2, 3, 4 or 5;
- f is 0, 1 or 2;
- g is 0, 1 or 2;
- h is 0, 1, 2, 3 or 4.

Preferred and/or optional features of the invention are set out below. Any aspect of the invention may be combined with any other aspect of the invention, unless the context demands otherwise. Any of the preferred or optional features of any aspect may be combined, singly or in combination, with any aspect of the invention, unless the context demands otherwise.

Definitions

The point of attachment of a moiety or substituent is represented by "-". For example, —OH is attached through the oxygen atom.

"Alkyl" refers to a straight-chain or branched saturated hydrocarbon group. In certain embodiments, the alkyl group may have from 1-20 carbon atoms, in certain embodiments from 1-15 carbon atoms, in certain embodiments, 1-8 carbon atoms. The alkyl group may be unsubstituted. Alternatively, the alkyl group may be substituted. Unless otherwise specified, the alkyl group may be attached at any suitable carbon atom and, if substituted, may be substituted at any suitable atom. Typical alkyl groups include but are not limited to methyl, ethyl, n-propyl, iso-propyl, n-butyl, iso-butyl, sec-butyl, tert-butyl, n-pentyl, n-hexyl and the like.

The term "cycloalkyl" is used to denote a saturated carbocyclic hydrocarbon radical. In certain embodiments, the cycloalkyl group may have from 3-15 carbon atoms, in certain embodiments, from 3-10 carbon atoms, in certain embodiments, from 3-8 carbon atoms. The cycloalkyl group may unsubstituted. Alternatively, the cycloalkyl group may be substituted. Unless other specified, the cycloalkyl group may be attached at any suitable carbon atom and, if substituted, may be substituted at any suitable atom. Typical cycloalkyl groups include but are not limited to cyclopropyl, cyclobutyl, cyclopentyl, cyclohexyl and the like.

"Alkoxy" refers to an optionally substituted group of the formula alkyl-O— or cycloalkyl-O—, wherein alkyl and cycloalkyl are as defined above.

"Aryl" refers to an aromatic carbocyclic group. The aryl group may have a single ring or multiple condensed rings. In certain embodiments, the aryl group can have from 6-20 carbon atoms, in certain embodiments from 6-15 carbon atoms, in certain embodiments, 6-12 carbon atoms. The aryl group may be unsubstituted. Alternatively, the aryl group may be substituted. Unless otherwise specified, the aryl group may be attached at any suitable carbon atom and, if substituted, may be substituted at any suitable atom. Examples of aryl groups include, but are not limited to, phenyl, naphthyl, anthracenyl and the like.

"Arylalkyl" refers to an optionally substituted group of the formula aryl-alkyl-, where aryl and alkyl are as defined above.

"Halo", "hal" or "halide" refers to —F, —Cl, —Br and —I.

"Heteroalkyl" refers to a straight-chain or branched saturated hydrocarbon group wherein one or more carbon atoms are independently replaced with one or more heteroatoms (e.g. nitrogen, oxygen, phosphorus and/or sulfur atoms). In certain embodiments, the heteroalkyl group may have from 1-20 carbon atoms, in certain embodiments from 1-15 carbon atoms, in certain embodiments, 1-8 carbon atoms. The heteroalkyl group may be unsubstituted. Alternatively, the heteroalkyl group may substituted. Unless otherwise specified, the heteroalkyl group may be attached at any suitable atom and, if substituted, may be substituted at any suitable atom. Examples of heteralkyl groups include but are not limited to ethers, thioethers, primary amines, secondary amines, tertiary amines and the like.

"Heterocycloalkyl" refers to a saturated cyclic hydrocarbon group wherein one or more carbon atoms are independently replaced with one or more heteroatoms (e.g. nitrogen, oxygen, phosphorus and/or sulfur atoms). In certain embodiments, the heterocycloalkyl group may have from 2-20 carbon atoms, in certain embodiments from 2-10 carbon atoms, in certain embodiments, 2-8 carbon atoms. The heterocycloalkyl group may be unsubstituted. Alternatively, the heterocycloalkyl group may be substituted. Unless otherwise specified, the heterocycloalkyl group may be attached at any suitable atom and, if substituted, may be substituted at any suitable atom. Examples of heterocycloalkyl groups include but are not limited to epoxide, morpholinyl, piperadinyl, piperazinyl, thirranyl, pyrrolidinyl, pyrazolidinyl, imidazolidinyl, thiazolidinyl, thiomorpholinyl and the like.

"Heteroaryl" refers to an aromatic carbocyclic group wherein one or more carbon atoms are independently replaced with one or more heteroatoms (e.g. nitrogen, oxygen, phosphorus and/or sulfur atoms). In certain embodiments, the heteroaryl group may have from 3-20 carbon atoms, in certain embodiments from 3-15 carbon atoms, in certain embodiments, 3-8 carbon atoms. The heteroaryl group may be unsubstituted. Alternatively, the heteroaryl group may substituted. Unless otherwise specified, the heteroaryl group may be attached at any suitable atom and, if substituted, may be substituted at any suitable atom. Examples of heteroaryl groups include but are not limited to thienyl, furanyl, pyrrolyl, imidazolyl, pyrazolyl, thiazolyl, isothiazolyl, oxazolyl, isoxazolyl, triazolyl, thiadiazolyl, thiophenyl, oxadiazolyl, pyridinyl, pyrimidyl, benzoxazolyl, benzthiazolyl, benzimidazolyl, indolyl, quinolinyl and the like.

"Substituted" refers to a group in which one or more hydrogen atoms are each independently replaced with substituents (e.g. 1, 2, 3, 4, 5 or more) which may be the same or different. Examples of substituents include but are not limited to -halo, —C(halo)$_3$, —R$^a$, —O—R$^a$, —S—R$^a$, —NR$^a$R$_b$, —CN, —C(O)—R$^a$, COOR$^a$, —C(S)—R$^a$, —C(S)OR$^a$, —S(O)$_2$OH, —S(O)$_2$—R$^a$, —S(O)$_2$NR$^a$R$^b$ and —CONR$^a$R$^b$, preferably -halo, —C(halo)$_3$, —R$^a$, —O—R$^a$, —NR$^a$R$^b$, —COOR$^a$ and —CONR$^a$R$^b$. R$^a$ and R$^b$ are independently selected from the groups consisting of H, alkyl, aryl, arylalkyl, heteroalkyl, heteroaryl, or R$^a$ and R$^b$ together with the atom to which they are attached form a heterocycloalkyl group, and wherein R$^a$ and R$^b$ may be unsubstituted or further substituted as defined herein.

"Metallocenyl" refers to a transition metal complex group wherein a transition metal atom or ion is "sandwiched" between two rings of atoms. The metallocenyl group may be substituted. Alternatively, the metallocenyl group may be unsubstituted. Unless otherwise specified, the metallocenyl group may be attached at any suitable atom and, if substituted, may be substituted at any suitable atom. Examples of transition metal atoms or ions include but are not limited to chromium, manganese, cobalt nickel and iron. An example of a suitable ring of atoms is a cyclopentadienyl ring. An example of a metallocenyl group includes but is not limited to ferrocenyl, which comprises a Fe(II) ion sandwiched between two cyclopentadienyl rings, wherein each cyclopentadienyl ring may be independently unsubstituted or substituted.

DETAILED DESCRIPTION

In one aspect, the invention provides a process for the preparation of an [M(X)$_2$(L$^1$)$_m$(L$^2$)] complex, the process comprising the step of:
reacting an [M(X)$_2$(L)$_3$] complex with a phosphorus ligand L$^1$ and a bidentate N,N ligand L$^2$ in a ketone solvent to form the [M(X)$_2$(L$^1$)$_m$(L$^2$)] complex;
wherein,
M is ruthenium or osmium;
X is an anionic ligand;
L is a monodentate phosphorus ligand;
L$^1$ is a monodentate phosphorus ligand which is different to L, or a bidentate phosphorus ligand;
m is 1 or 2, wherein,
when m is 1, L$^1$ is a bidentate phosphorus ligand;
when m is 2, each L$^1$ is a monodentate phosphorus ligand; and
L$^2$ is a bidentate N,N ligand comprising a nitrogen-containing heteroaryl group and an amino group.

The metal M is a platinum group metal selected from ruthenium or osmium.

In one embodiment, M is ruthenium. When M is ruthenium, M may be Ru(II). In another embodiment, M is osmium. When M is osmium, M may be Os(II).

X is an anionic ligand, preferably a halide, such as —Cl, —Br and —I. Preferably, X is —Cl.

L is a monodentate phosphorus ligand and each L may be the same or different. Preferably, L is a tertiary phosphine ligand PR$_1$R$_2$R$_3$. R$_1$, R$_2$ and R$_3$ may be independently selected from the group consisting of unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl and substituted C$_{4-20}$-heteroaryl. R$_1$, R$_2$ and R$_3$ may be independently substituted or unsubstituted branched- or straight-chain alkyl groups such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly, or aryl groups such as phenyl, naphthyl or anthracyl. In one embodiment, the alkyl groups may be optionally substituted with one or more substituents such as halide (F, Cl, Br or I) or alkoxy groups, e.g. methoxy, ethoxy or propoxy.

The aryl group may be optionally substituted with one or more (e.g. 1, 2, 3, 4, or 5) substituents such as halide (—F, —Cl, —Br or —I), straight- or branched-chain C$_1$-C$_{10}$-alkyl (e.g. methyl), C$_1$-C$_{10}$ alkoxy, straight- or branched-chain C$_{1-10}$-(dialkyl)amino, C$_{3-10}$ heterocycloalkyl groups (such as morpholinyl and piperadinyl) or tri(halo)methyl (e.g. F$_3$C—). Substituted or unsubstituted heteroaryl groups such as pyridyl may also be used. In an alternative embodiment, any two of R$_1$, R$_2$ and R$_3$ may be linked to form a ring structure with the phosphorus atom, preferably 4- to 7-membered rings. Preferably, R$_1$, R$_2$ and R$_3$ are the same and are phenyl i.e. PR$_1$R$_2$R$_3$ is triphenylphosphine. Alternatively, R$_1$, R$_2$ and R$_3$ may be the same and are tolyl i.e. PR$_1$R$_2$R$_3$ is tritolylphosphine (e.g. ortho-, meta- or para-tritolylphosphine).

In one embodiment, the [M(X)$_2$(L)$_3$] complex may be a [ruthenium (Hal)$_2$ (PR$_1$R$_2$R$_3$)$_3$] complex, wherein R$_1$, R$_2$ and R$_3$ are independently selected from unsubstituted C$_{5-20}$-aryl and substituted C$_{5-20}$-aryl. In one preferred embodiment, the [M(X)$_2$(L)$_3$] complex may be [RuCl$_2$ (PPh$_3$)$_3$]. In another preferred embodiment, the [M(X)$_2$(L)$_3$] complex may be [RuCl$_2$ (P(tolyl)$_3$)$_3$].

In another embodiment, the [M(X)$_2$(L)$_3$] complex may be an [osmium (Hal)$_2$ (PR$_1$R$_2$R$_3$)$_3$] complex, wherein R$_1$, R$_2$ and R$_3$ are independently selected from unsubstituted C$_{5-20}$-aryl and substituted C$_{5-20}$-aryl. In one preferred embodiment, the [M(X)$_2$(L)$_3$] complex may be [Os Cl$_2$ (PPh$_3$)$_3$]. In another preferred embodiment, the [M(X)$_2$(L)$_3$] complex may be [Os Cl$_2$ (P(tolyl)$_3$)$_3$].

L$^1$ is a monodentate phosphorus ligand which is different to L. In this instance, m is 2. Alternatively,
L$^1$ is a bidentate phosphorus ligand and, in this instance, m is 1.

Any suitable phosphorus compound capable of forming a ligand-metal interaction with the M atom may be used. In the ligand, each phosphorus atom is covalently bonded to either 3 carbon atoms (tertiary phosphines) or to n heteroatoms and 3-n carbon atoms, where n=1, 2 or 3. Preferably, the heteroatom is selected from the group consisting of N and O.

The phosphorus ligand may be monodentate, e.g. PPh₃, or bidentate. The ligand may be chiral or achiral, although in many instances it is preferred that the phosphorus ligand is chiral. A variety of chiral phosphorus ligands has been described and reviews are available, for example see W. Tang and X. Zhang, Chem Rev. 2003, 103, 3029-3070 and J. C. Carretero, Angew. Chem. Int. Ed., 2006, 45, 7674-7715. Phosphorus ligands that may be used in the present invention include but are not restricted to the following structural types:

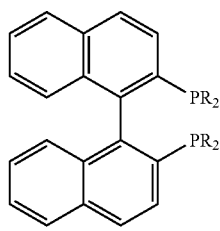

BINAP, R = aryl and alkyl

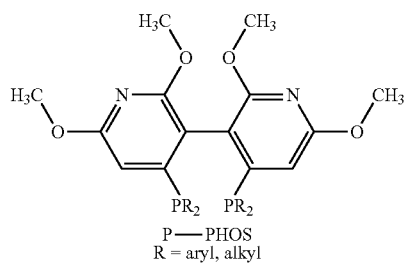

P—PHOS
R = aryl, alkyl

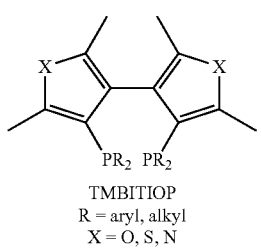

TMBITIOP
R = aryl, alkyl
X = O, S, N

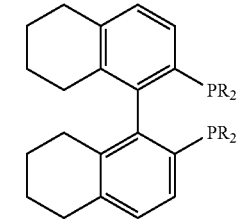

H⁸—BINAP, R = aryl and alkyl

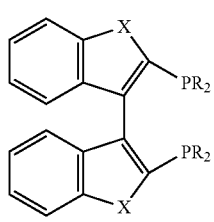

BITIANAP
R = aryl, alkyl
X = O, S, N

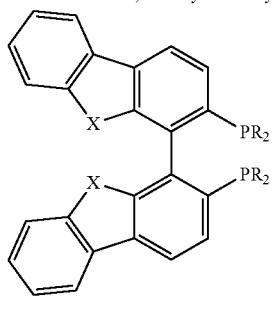

R = aryl, alkyl
X = O BIBFUP
X = NH or S

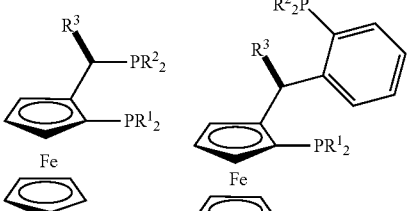

JOSIPHOS
R¹ = alkyl, aryl
R² = alkyl, aryl
R³ = alkyl, aryl

TANIAPHOS
R¹ = alkyl, aryl
R² = alkyl, aryl
R³ = alkyl

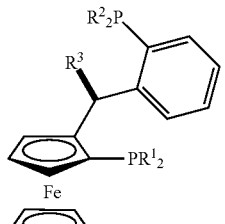

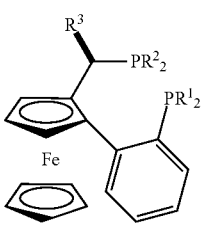

WALPHOS
R¹ = alkyl, aryl
R² = alkyl, aryl

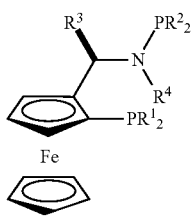

BOPHOZ
R¹ = alkyl, aryl
R² = alkyl, aryl, Oalkyl, Oaryl
R³ = alkyl, aryl
R⁴ = alkyl, aryl

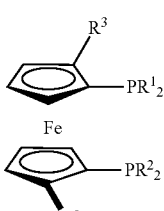 including

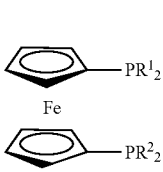

DIPFC: R¹ = R² = sec Pr
DCyPFC: R¹ = R² = Cy

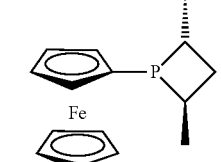

Me-FERROTANE

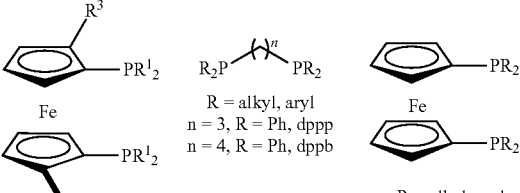

FERROPHOS
R¹ = alkyl, aryl
R³ = 3-pentyl

R = alkyl, aryl
n = 3, R = Ph, dppp
n = 4, R = Ph, dppb

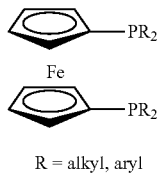

R = alkyl, aryl
R = Ph, dppf

-continued

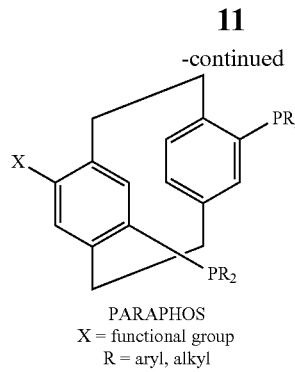

PARAPHOS
X = functional group
R = aryl, alkyl

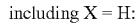 including X = H:

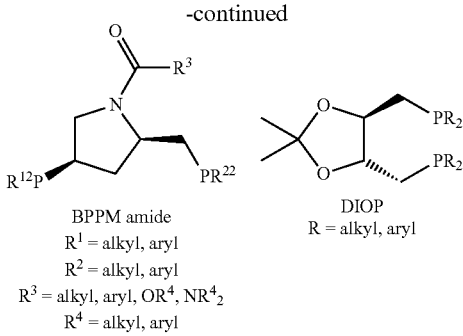

BPPM amide
$R^1$ = alkyl, aryl
$R^2$ = alkyl, aryl
$R^3$ = alkyl, aryl, $OR^4$, $NR^4{}_2$
$R^4$ = alkyl, aryl DIOP
R = alkyl, aryl

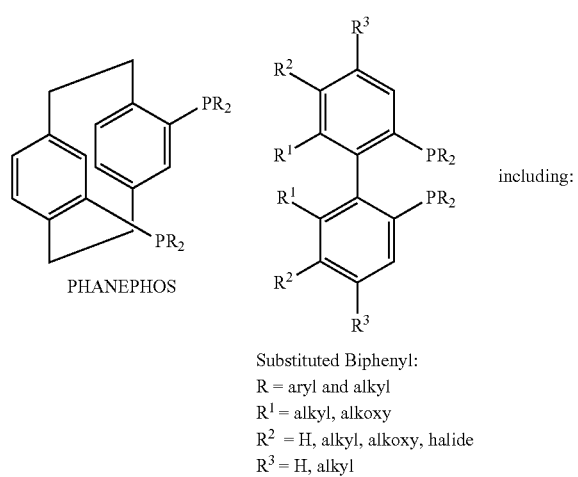

PHANEPHOS

Substituted Biphenyl:
R = aryl and alkyl
$R^1$ = alkyl, alkoxy
$R^2$ = H, alkyl, alkoxy, halide
$R^3$ = H, alkyl including:

In the above structures —$PR_2$ may be —$P(alkyl)_2$ in which alkyl is preferably $C_1$-$C_{10}$ alkyl, —$P(aryl)_2$ where aryl includes phenyl and naphthyl which may be substituted or unsubstituted or —$P(O-alkyl)_2$ and —$P(O-aryl)_2$ with alkyl and aryl as defined above. —$PR_2$ may also be substituted or unsubstituted —$P(heteroaryl)_2$, where heteroaryl includes furanyl (e.g. 2-furanyl or 3-furanyl). —$PR_2$ is preferably either —$P(aryl)_2$ where aryl includes phenyl, tolyl, xylyl or anisyl or —$P(O-aryl)_2$. If —$PR_2$ is —$P(O-aryl)_2$, the most preferred O-aryl groups are those based on chiral or achiral substituted 1,1'-biphenol and 1,1'-binaphtol. Alternatively, the R groups on the P-atom may be linked as part of a cyclic structure.

Substituting groups may be present on the alkyl or aryl substituents in the phosphorus ligands. Such substituting groups are typically branched or linear $C_{1-6}$ alkyl groups such as methyl, ethyl, propyl, isopropyl, tert butyl and cyclohexyl.

The phosphorus ligands are preferably used in their single enantiomer form. These phosphorus ligands are generally available commercially and their preparation is known. For example, the preparation of PARAPHOS ligands is given in WO 04/111065, the preparation of Bophoz ligands in WO02/26750 and U.S. Pat. No. 6,906,212 and the preparation of Josiphos ligands in EP564406B and EP612758B.

The phosphorus ligand $L^1$ preferably includes Binap ligands, PPhos ligands, PhanePhos ligands, QPhos ligands, Josiphos ligands and Bophoz ligands.

When $L^1$ is a Binap ligand, the ligand may be of formula (Ia) or (Ia):

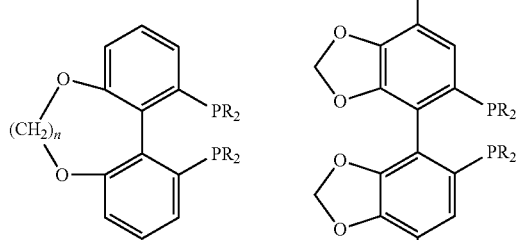

$C_n$ TUNAPHOS
$R^1$ = OMe: BIPHEP
$R^1$ = OMe, $R^2$ = Cl: Cl, MeO BIPHEP
$R^1$ and $R^3$ = Me, $R^2$ = OMe: BIMOP
$R^1$ = Me: BIPHEMP
$R^1$ and $R^3$ = Me: TETRAPHEMP
$R^1$, $R^2$ and $R^3$ = Me: HEXAPHEMP

SEGPHOS

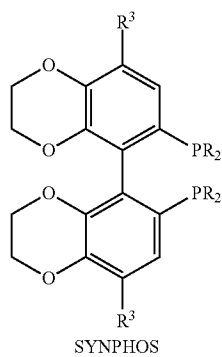

SYNPHOS

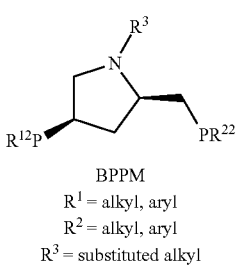

BPPM
$R^1$ = alkyl, aryl
$R^2$ = alkyl, aryl
$R^3$ = substituted alkyl

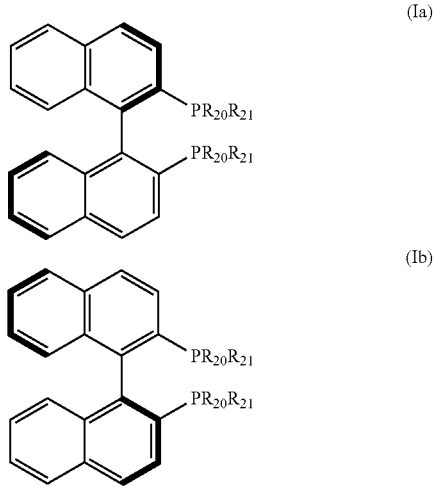

(Ia)

(Ib)

wherein,
R$_{20}$ and R$_{21}$ are each independently selected from the group consisting of unsubstituted C$_{3-20}$-cycloalkyl, substituted C$_{3-20}$-cycloalkyl, unsubstituted C$_{5-20}$-aryl and substituted C$_{5-20}$-aryl. In one embodiment, R$_{20}$ and R$_{21}$ are each independently selected from the group consisting of cycloalkyl groups such as cyclopropyl, cyclobutyl, cyclopentyl, cyclohexyl or adamantly, or aryl groups such as phenyl, naphthyl or anthracyl. In one embodiment, the cycloalkyl groups may be optionally substituted with one or more substituents such as halide (F, Cl, Br or I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain C$_1$-C$_{10}$-alkyl (e.g. methyl), C$_1$-C$_{10}$ alkoxy, straight- or branched-chain C$_1$-C$_{10}$-(dialkyl)amino, C$_{3-10}$ heterocycloalkyl groups (such as morpholinyl and piperadinyl) or tri(halo)methyl (e.g. F$_3$C—). Preferably, R$_{20}$ and R$_{21}$ are the same and are selected from the group consisting of phenyl, tolyl (o-, m- or p-, preferably p-tolyl) and xylyl (e.g. 3,5-xylyl).

When L$^1$ is a Josiphos ligand, the ligand may be of formula (IIa) or (IIb):

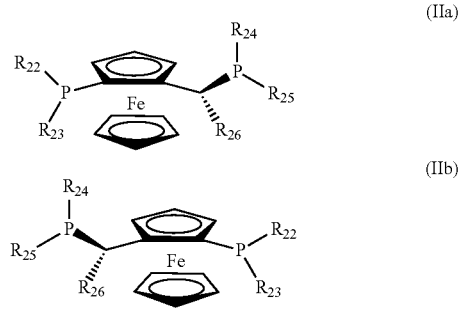

wherein,
R$_{22}$ and R$_{23}$ are independently selected from the group consisting of unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl and substituted C$_{4-20}$-heteroaryl;
R$_{24}$ and R$_{25}$ are independently selected from the group consisting of unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl and substituted C$_{4-20}$-heteroaryl; and
R$_{26}$ is selected from the group consisting of unsubstituted C$_{1-20}$-alkyl and substituted C$_{1-20}$-alkyl.

In one embodiment, R$_{22}$ and R$_{23}$ are independently selected from the group consisting of substituted or unsubstituted branched- or straight-chain alkyl groups such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly, aryl groups such as phenyl, naphthyl or anthracyl and heteroaryl groups such as furyl. In one embodiment, the alkyl groups may be optionally substituted with one or more substituents such as halide (F, Cl, Br or I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain C$_1$-C$_{10}$-alkyl (e.g. methyl), C$_1$-C$_{10}$ alkoxy, straight- or branched-chain C$_1$-C$_{10}$-(dialkyl)amino, C$_{3-10}$ heterocycloalkyl groups (such as morpholinyl and piperadinyl) or tri(halo)methyl (e.g. F$_3$C—). The heteroaryl group may be optionally substituted with one or more (e.g. 1, 2, 3, 4, or 5) substituents such as halide (—F, —Cl, —Br or —I), straight- or branched-chain C$_1$-C$_{10}$-alkyl (e.g. methyl), C$_1$-C$_{10}$ alkoxy, straight- or branched-chain C$_1$-C$_{10}$-(dialkyl)amino or tri(halo)methyl (e.g. F$_3$C—). Preferably, R$_{22}$ and R$_{23}$ are the same and are selected from the group consisting of tert-butyl, cyclohexyl, phenyl, 3,5-bis(trifluoromethyl)phenyl, 4-methoxy-3,5-dimethylphenyl, 4-trifluoromethylphenyl, 1-naphthyl, 3,5-xylyl, 2-methylphenyl and 2-furyl, most preferably tert-butyl, cyclohexyl, phenyl, 3,5-bis(trifluoromethyl)phenyl, 4-methoxy-3,5-dimethylphenyl, 4-trifluoromethylphenyl, 1-naphthyl and 2-furyl.

In one embodiment, R$_{24}$ and R$_{25}$ are independently selected from the group consisting of substituted or unsubstituted branched- or straight-chain alkyl groups such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly, aryl groups such as phenyl, naphthyl or anthracyl and heteroaryl groups such as furyl. In one embodiment, the alkyl groups may be optionally substituted with one or more substituents such as halide (F, Cl, Br or I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain C$_1$-C$_{10}$-alkyl (e.g. methyl), C$_1$-C$_{10}$ alkoxy, straight- or branched-chain C$_1$-C$_{10}$-(dialkyl)amino, C$_{3-10}$ heterocycloalkyl groups (such as morpholinyl and piperadinyl) or tri(halo)methyl (e.g. F$_3$C—). The heteroaryl group may be optionally substituted with one or more (e.g. 1, 2, 3, 4, or 5) substituents such as halide (—F, —Cl, —Br or —I), straight- or branched-chain C$_1$-C$_{10}$-alkyl (e.g. methyl), C$_1$-C$_{10}$ alkoxy, straight- or branched-chain C$_1$-C$_{10}$-(dialkyl)amino or tri(halo)methyl (e.g. F$_3$C—). Preferably, R$_{24}$ and R$_{25}$ are the same and are selected from the group consisting of tert-butyl, cyclohexyl, phenyl, 3,5-bis(trifluoromethyl)phenyl, 4-methoxy-3,5-dimethylphenyl, 4-trifluoromethylphenyl, 1-naphthyl, 3,5-xylyl, 2-methylphenyl and 2-furyl, most preferably tert-butyl, cyclohexyl, phenyl, 3,5-xylyl and 2-methylphenyl.

In one embodiment, R$_{26}$ is an unsubstituted branched- or straight-chain alkyl groups such as methyl, ethyl, n-propyl, iso-propyl, n-butyl, iso-butyl, sec-butyl, tert-butyl, pentyl, hexyl, heptyl, octyl, nonyl, decyl, dodecyl or stearyl. Preferable, R$_{26}$ is methyl.

In one embodiment, the ligand of formula (IIa) is selected from the group consisting of:
(R)-1-[(S)-2-di(phenylphosphino)ferrocenyl]ethyldicyclohexylphosphine,
(R)-1-[(S)-2-di(phenylphosphino)ferrocenyl]ethyldi-tert-butylphosphine,
(R)-1-[(S)-2-di(cyclohexylphosphino)ferrocenyl]ethyldicyclohexylphosphine, (R)-1-[(S)-2-di(cyclohexylphosphino)ferrocenyl]ethyldiphenylphosphine,
(R)-1-[(S)-2-di(phenylphosphino)ferrocenyl]ethyldi-3,5-xylylphosphine,
(R)-1-[(S)-2-di-(3,5-bis(trifluoromethyl)phenylphosphino)ferrocenyl]ethyldicyclohexylphosphine,
(R)-1-[(S)-2-di-(4-methoxy-3,5-dimethyl)phenylphosphino)ferrocenyl]ethyldicyclohexylphosphine,
(R)-1-[(S)-2-di-(3,5-bis(trifluoromethyl)phenylphosphino)ferrocenyl]ethyldi-3,5-xylylphosphine,
(R)-1-[(S)-2-di(cyclohexylphosphino)ferrocenyl]ethyldi-tert-butylphosphine,
(R)-1-[(S)-2-di-((4-trifluoromethyl)phenylphosphino)ferrocenyl]ethyldi-tert-butylphosphine,
(R)-1-[(S)-2-di-(4-methoxy-3,5-dimethyl)phenylphosphino)ferrocenyl]ethyldi-tert-butylphosphine,
(R)-1-[(S)-2-di-(2-furyl)phosphino)ferrocenyl]ethyldi-3,5-xylylphosphine,
(R)-1-[(S)-2-di-(2-furyl)phosphino)ferrocenyl]ethyldi-tert-butylphosphine,
(R)-1-[(S)-2-di(1-naphthyl)phosphino)ferrocenyl]ethyldi-tert-butylphosphine,
(R)-1-[(S)-2-di(1-naphthyl)phosphino)ferrocenyl]ethyldi-3,5-xylylphosphine,
(R)-1-[(S)-2-di-(4-methoxy-3,5-dimethyl)phenylphosphino)ferrocenyl]ethyldi-3,5-xylylphosphine,
(R)-1-[(S)-2-di-(4-methoxy-3,5-dimethyl)phenylphosphino)ferrocenyl]ethyldi-(2-methylphenyl)phosphine,
(R)-1-[(S)-2-di-(2-furyl)phosphinoferrocenyl]ethyldi-(2-methylphenyl)phosphine,
(R)-1-[(S)-2-di(tert-butylphosphino)ferrocenyl]ethyldiphenylphosphine,
(R)-1-[(S)-2-di(tert-butylphosphino)ferrocenyl]ethyldi-(2-methylphenyl)phosphine, and
(R)-1-[(S)-2-diphenylphosphinoferrocenyl]ethyldiphenylphosphine.

In one embodiment, the ligand of formula (IIIb) is selected from the group consisting of:
(S)-1-[(R)-2-di(phenylphosphino)ferrocenyl]ethyldicyclohexylphosphine,
(S)-1-[(R)-2-di(phenylphosphino)ferrocenyl]ethyldi-tert-butylphosphine,
(S)-1-[(R)-2-di(cyclohexylphosphino)ferrocenyl]ethyldicyclohexylphosphine,
(S)-1-[(R)-2-di(cyclohexylphosphino)ferrocenyl]ethyldiphenylphosphine,
(S)-1-[(R)-2-di(phenylphosphino)ferrocenyl]ethyldi-3,5-xylylphosphine,
(S)-1-[(R)-2-di-(3,5-bis(trifluoromethyl)phenylphosphino)ferrocenyl]ethyldicyclohexylphosphine,
(S)-1-[(R)-2-di-(4-methoxy-3,5-dimethyl)phenylphosphino)ferrocenyl]ethyldicyclohexylphosphine,
(S)-1-[(R)-2-di-(3,5-bis(trifluoromethyl)phenylphosphino)ferrocenyl]ethyldi-3,5-xylylphosphine,
(S)-1-[(R)-2-di(cyclohexylphosphino)ferrocenyl]ethyldi-tert-butylphosphine,
(S)-1-[(R)-2-di-((4-trifluoromethyl)phenylphosphino)ferrocenyl]ethyldi-tert-butylphosphine,
(S)-1-[(R)-2-di-(4-methoxy-3,5-dimethyl)phenylphosphino)ferrocenyl]ethyldi-tert-butylphosphine,
(S)-1-[(R)-2-di-(2-furyl)phosphino)ferrocenyl]ethyldi-3,5-xylylphosphine,
(S)-1-[(R)-2-di-(2-furyl)phosphino)ferrocenyl]ethyldi-tert-butylphosphine,
(S)-1-[(R)-2-di(1-naphthyl)phosphino)ferrocenyl]ethyldi-tert-butylphosphine,
(S)-1-[(R)-2-di(1-naphthyl)phosphino)ferrocenyl]ethyldi-3,5-xylylphosphine,
(S)-1-[(R)-2-di-(4-methoxy-3,5-dimethyl)phenylphosphino)ferrocenyl]ethyldi-3,5-xylylphosphine,
(S)-1-[(R)-2-di-(4-methoxy-3,5-dimethyl)phenylphosphino)ferrocenyl]ethyldi-(2-methylphenyl)phosphine,
(S)-1-[(R)-2-di-(2-furyl)phosphinoferrocenyl]ethyldi-(2-methylphenyl)phosphine,
(S)-1-[(R)-2-di(tert-butylphosphino)ferrocenyl]ethyldiphenylphosphine,
(S)-1-[(R)-2-di(tert-butylphosphino)ferrocenyl]ethyldi-(2-methylphenyl)phosphine, and
(S)-1-[(R)-2-diphenylphosphinoferrocenyl]ethyldiphenylphosphine.

In one preferred embodiment, the ligand of formula (IIa) is (R)-1-[(S)-2-diphenylphosphinoferrocenyl]ethyldiphenylphosphine. In another preferred embodiment, the ligand of formula (IIb) is (S)-1-[(R)-2-diphenylphosphinoferrocenyl]ethyldiphenylphosphine.

The phosphorus ligand $L^1$ also preferably includes $PPh_3$, $PCy_3$ (tricyclohexylphosphine), dppf (1,1'-bis(diphenylphosphino)ferrocene), dppp (1,3-bis(diphenylphosphino)propane), dppb (1,4-bis(diphenylphosphino)butane), Dipfc (1,1'-bis(di-isopropylphosphino)ferrocene), dCyPfc (1,1'-bis(di-cyclohexylphosphino)ferrocene and DB$^t$PF (1,1'-bis(di-tert-butylphosphino)ferrocene). In one embodiment, the phosphorus ligand $L^1$ is unsubstituted. In another embodiment, the ligand $L^1$ is substituted.

Particularly preferred phosphorus ligands $L^1$ may be selected from the group consisting of dppf, dppp, dppb and dCyPfc.

$L^2$ is a bidentate N,N ligand comprising a nitrogen-containing heteroaryl group and an amino group. The nitrogen-containing heteroaryl group may include a pyridinyl, pyrrolyl, imidazolyl, pyrazolyl, pyrimidyl, indolyl or quinolinyl groups, preferably pyridinyl. The amino group may comprise primary, secondary or tertiary amino groups, preferably $-NH_2$.

The bidentate N,N-ligand may selected from the group consisting of ligands (1), (2) and (3):

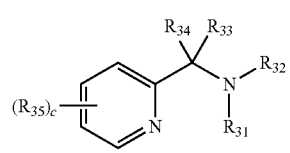
(1)

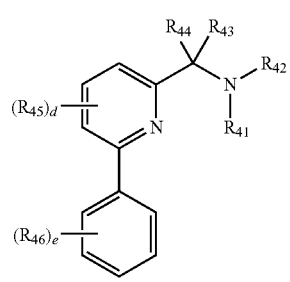
(2)

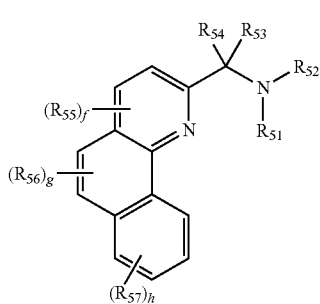

(3)

In one embodiment, the bidentate N,N-ligand is ligand (1). In another embodiment, the bidentate N,N-ligand is ligand (2). In yet another embodiment, the bidentate N,N-ligand is ligand (3).

The bidentate N,N ligands of formulae (1), (2) or (3) may be added to the reaction mixture as the free base or as a salt (e.g. the hydrochloride salt). When a salt is used, however, the reaction mixture may also comprise a base (such as triethylamine) in order to form the free base.

Ligands (1), (2) and (3) are bidentate ligands as each ligand coordinates to the M atom through the amino and pyridino functional groups.

$R_{31}$ and $R_{32}$ may be independently selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. Preferably, $R_{31}$ and $R_{32}$ are independently selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as —H, methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly, or aryl groups such as phenyl, naphthyl or anthracyl. In one embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_{1-10}$-(dialkyl)amino, $C_{3-10}$ heterocycloalkyl groups (such as morpholinyl and piperadinyl) or tri(halo)methyl (e.g. $F_3C$—).

In one embodiment, one of $R_{31}$ and $R_{32}$ is —H and the other is selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. In one preferred embodiment, one of $R_{31}$ and $R_{32}$ is —H and the other is selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as —H, methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly, or aryl groups such as phenyl, naphthyl or anthracyl. In one embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_{1-10}$-(dialkyl)amino, $C_{3-10}$ heterocycloalkyl groups (such as morpholinyl and piperadinyl) or tri(halo)methyl (e.g. $F_3C$—).

In one preferred embodiment, $R_{31}$ and $R_{32}$ are both —H. $R_{33}$ and $R_{34}$ may be the same or different. When $R_{33}$ and $R_{34}$ are different, the ligand (1) will contain chiral centre. The ligand (1) can be used as a racemic mixture, as either single enantiomer or as a mixture of enantiomers, preferably as a single enantiomer. The enantiomers of ligand (1) may be obtained in enantiomerically pure form by resolution of e.g. a racemic mixture of ligand (1).

$R_{33}$ and $R_{34}$ may be independently selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. Preferably, $R_{31}$ and $R_{32}$ are independently selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as —H, methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly, or aryl groups such as phenyl, naphthyl or anthracyl. In one embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3C$—). More preferably, $R_{33}$ and $R_{34}$ are independently selected from —H, methyl, ethyl, n-propyl, iso-propyl, n-butyl, iso-butyl, sec-butyl, tert-butyl and phenyl.

In one embodiment, one of $R_{33}$ and $R_{34}$ is —H and the other is selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. In one preferred embodiment, one of $R_{33}$ and $R_{34}$ is —H and the other is selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as —H, methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly, or aryl groups such as phenyl, naphthyl or anthracyl. In one embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_{1-10}$-(dialkyl)amino, $C_{3-10}$ heterocycloalkyl groups (such as morpholinyl and piperadinyl) or tri(halo)methyl (e.g. $F_3C$—). More preferably, $R_{33}$ and $R_{34}$ are independently selected from —H, methyl, ethyl, n-propyl, iso-propyl, n-butyl, iso-butyl, sec-butyl, tert-butyl and phenyl. Most preferably, one of $R_{33}$ and $R_{34}$ is —H and the other of $R_{33}$ and $R_{34}$ is selected from the group of consisting of —H, methyl, ethyl, n-propyl, iso-propyl, n-butyl, iso-butyl, sec-butyl, tert-butyl and phenyl.

$R_{35}$ may be present or absent. When absent, c is 0 i.e. the pyridine ring is not substituted. When $R_{35}$ is present, c may be 1, 2, 3 or 4. When c is 2, 3 or 4, each $R_{35}$ may be the same or different to each other. The or each $R_{35}$ may be independently selected from the group consisting of unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. Preferably, $R_{35}$ is independently selected from the group consisting of unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly, or aryl groups such as phenyl, naphthyl or anthracyl. In one embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3C$—). Preferably, c is 0 i.e. $R_{35}$ is absent and the pyridine ring is unsubstituted.

$R_{41}$ and $R_{42}$ may be independently selected from the groups described above for $R_{31}$ and $R_{32}$.

$R_{43}$ and $R_{44}$ may be the same or different. When $R_{43}$ and $R_{44}$ are different, the ligand (2) will contain chiral centre. The ligand (2) can be used as a racemic mixture, as either single enantiomer or as a mixture of enantiomers, preferably as a single enantiomer. The enantiomers of ligand (2) may be obtained in enantiomerically pure form by resolution of e.g. a racemic mixture of ligand (2). $R_{43}$ and $R_{44}$ may be independently selected from the groups as described above for $R_{33}$ and $R_{34}$.

$R_{45}$ may be present or absent. When absent, d is 0. When $R_{45}$ is present, d may be 1, 2 or 3. When d is 2 or 3, each $R_{45}$ may be the same or different to each other. The or each $R_{45}$ may be selected from the groups described above for $R_{35}$. Preferably, d is 0 i.e. $R_{45}$ is absent.

$R_{46}$ may be present or absent. When absent, e is 0. When $R_{46}$ is present, e may be 1, 2, 3, 4 or 5.

When d is 2, 3, 4 or 5, each $R_{46}$ may be the same or different to each other. The or each $R_{46}$ may be selected from the groups described above for $R_{35}$. In one preferred embodiment, e is 0 i.e. $R_{45}$ is absent. In another preferred embodiment, $R_{46}$ is 1 and is selected from the group consisting of methyl, ethyl, n-propyl, iso-propyl, n-butyl, iso-butyl, sec-butyl and tert-butyl, preferably, 4-Me.

$R_{51}$ and $R_{52}$ may be independently selected from the groups described above for $R_{31}$ and $R_{32}$.

$R_{53}$ and $R_{54}$ may be the same or different. When $R_{53}$ and $R_{54}$ are different, the ligand (3) will contain chiral centre. The ligand (3) can be used as a racemic mixture, as either single enantiomer or as a mixture of enantiomers, preferably as a single enantiomer. The enantiomers of ligand (3) may be obtained in enantiomerically pure form by resolution of e.g. a racemic mixture of ligand (3). $R_{53}$ and $R_{54}$ may be independently selected from the groups as described above for $R_{33}$ and $R_{34}$.

$R_{55}$ may be present or absent. When absent, f is 0. When $R_{55}$ is present, f may be 1 or 2. When f is 2, each $R_{45}$ may be the same or different to the other. The or each $R_{55}$ may be selected from the groups described above for $R_{35}$. Preferably, f is 0 i.e. $R_{55}$ is absent.

$R_{56}$ may be present or absent. When absent, g is 0. When $R_{56}$ is present, g may be 1 or 2. When g is 2, each $R_{56}$ may be the same or different to each other. The or each $R_{56}$ may be selected from the groups described above for $R_{35}$. In one preferred embodiment, g is 0 i.e. $R_{56}$ is absent.

$R_{57}$ may be present or absent. When absent, h is 0. When $R_{57}$ is present, h may be 1, 2, 3 or 4. When d is 2, 3 or 4, each $R_{57}$ may be the same or different to each other. The or each $R_{57}$ may be selected from the groups described above for $R_{35}$. In one preferred embodiment, h is 0 i.e. $R_{57}$ is absent.

In one preferred embodiment, the bidentate N,N-ligand is selected from the group consisting of:

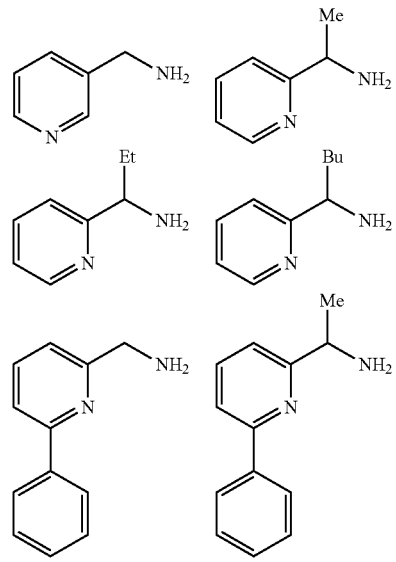

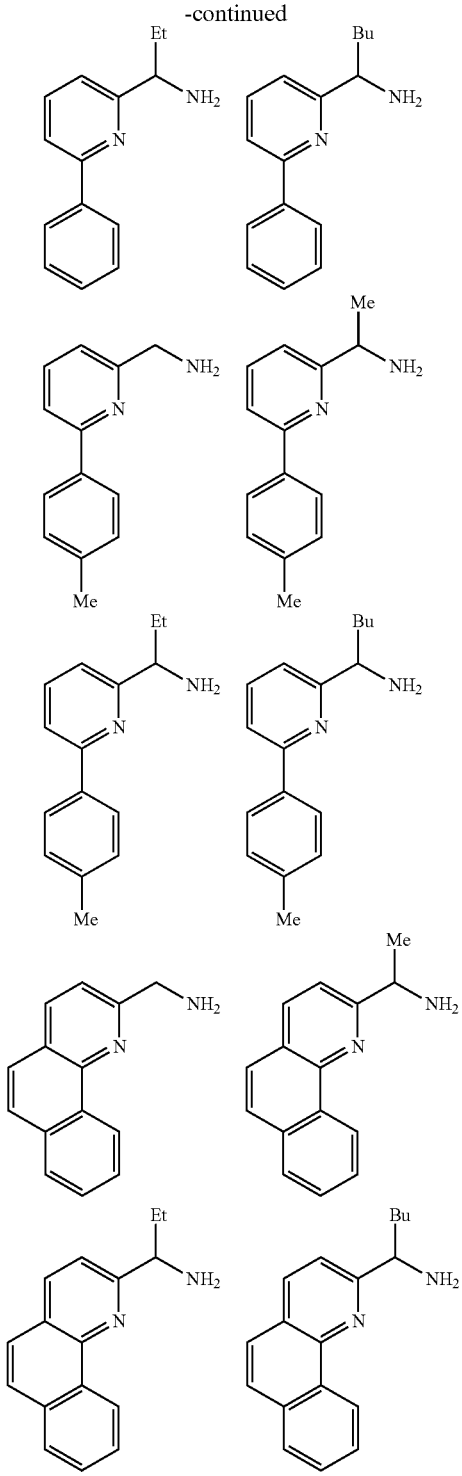

In one particularly preferred embodiment, the bidentate N,N-ligand is 2-aminomethylpyridine (AMPY).

In one preferred embodiment, the $[M(X)_2(L^1)_m(L^2)]$ complex may be selected from the group consisting of:
[RuCl$_2$ (dppp) AMPY];
[RuCl$_2$ (dppb) AMPY];
[RuCl$_2$ (dppf) AMPY];
[RuCl$_2$ (DCyPFc) AMPY];
[RuCl$_2$ (DiPFc) AMPY];
[RuCl$_2$ (DBtPFc) AMPY];
[RuCl$_2$ (Josiphos*) AMPY]; and
[RuCl$_2$ (TolBINAP) AMPY];

The $[M(X)_2(L)_3]$ complex is reacted with the phosphorus ligand $L^1$ and the bidentate N,N ligand $L^2$ in a ketone solvent to form the $[M(X)_2(L^1)_m(L^2)]$ complex. By "ketone solvent" we mean a liquid ketone which has a boiling point at atmospheric pressure (i.e. $1.0135 \times 10^5$ Pa) below 160° C. and more preferably below 120° C. Preferred examples are acetone, methyl-ethyl ketone (MEK) also known as 2-butanone, methyl-isobutyl ketone (MIBK) also known as 4-methyl-2-pentanone and diethylketone also known as 3-pentanone. A particularly preferred ketone solvent is MEK. Another particularly preferred ketone solvent is acetone.

There are several advantages associated with using a ketone solvent. One advantage is that ketone solvents such as acetone are non-chlorinated and have a low toxicological potential.

Another advantage is that reaction solvent volumes are reduced in comparison to the prior art solvents which use dichloromethane.

Furthermore, unlike prior art solvents which use toluene, the ketone solvents are generally easier to remove by evaporation. In addition, when the bidentate N,N-ligand $L^2$ is 2-aminomethylpyridine, the ketone solvents do not produce a paste-like product which takes an extended period of time to filter and does not dry into a ceramic-like product that requires further processing (e.g. by grinding) to produce a powder. All of these advantages are in contrast to the use of toluene.

In one embodiment of the process of the present invention, the complexes are slurried in the ketone solvent. "Slurry" means a heterogeneous mixture of at least a portion of the complex (or complexes) in the ketone solvent. "Slurry" therefore includes a mixture of a complex or complexes which are partially present as a solid, as well as being partially dissolved in the ketone solvent. The complexes which can be slurried include the $[M(X)_2(L)_3]$ starting material, intermediate metal complexes and/or the $[M(X)_2(L^1)_m(L^2)]$ product.

Yet another advantage is that the ketone solvent is capable of removing large quantities of the monodentate phosphorus ligand L which is released from the $[M(X)_2(L)_3]$ starting material during the reaction. For example, when [RuCl$_2$ (PPh$_3$)$_3$] is utilised as the starting material and acetone as the ketone solvent, substantially complete removal of PPh$_3$ can be obtained. In this respect, the metal complexes are generally in solid form in reaction mixture (because they form a slurry in the ketone solvent), while the ligand L is substantially dissolved in the ketone solvent, together with unreacted ligand $L^1$.

In contrast, when dichloromethane is used as a solvent, the reaction mixture is in solution as the components of the reaction have been dissolved. The product complex, therefore, typically requires precipitation from the reaction mixture. In this respect, dichloromethane/alcohol, dichloromethane/alkane or toluene/alkane solvent mixtures, generally result in large yield losses and/or the formation of impure products.

In another embodiment, the $[M(X)_2(L)_3]$ starting material forms a slurry with the ketone solvent but on reaction with the phosphorus ligand L or bidentate N,N ligand $L^2$ may form intermediate metal complexes and/or the $[M(X)_2(L^1)_m(L^2)]$ product which are soluble in the ketone solvent. In this instance, the ketone solvent is still capable of removing large quantities of the monodentate phosphorus ligand L which is released from the $[M(X)_2(L)_3]$ starting material during the reaction. If any solid [M(X)$_2$(L)$_3$] starting material remains on termination of the reaction, the [M(X)$_2$(L)$_3$] starting material may be separated from the soluble [M(X)$_2$ (L$^1$)$_m$ (L$^2$)] product by filtering, decanting or centrifuging.

Any suitable volume of ketone solvent may be used. For example, the ratio of ketone solvent to [M (X)$_2$ (L)$_3$] complex may be about 3-about 35 mL/g. In certain embodiments, the ratio may be about 3-about 20 mL/g. In certain embodiments, the ratio may be about 20-about 35 mL/g.

The reactants may be added in any suitable order, but in one preferred process of the invention, the phosphorus ligand L$^1$ may be added (e.g. portion wise) to a mixture of the [M(X)$_2$(L)$_3$] complex in the ketone solvent and, after stirring for a suitable period of time and at a suitable temperature, the bidentate N,N ligand L$^2$ may be added (e.g. portion wise). If desired, the bidentate N,N ligand L$^2$ may be added to the reaction mixture as a solution in ketone solvent. The reaction may then be stirred for a further suitable period of time and at a suitable temperature. If desired, the ketone solvent may be saturated with an inert gas (e.g. nitrogen) before it is added to the reaction mixture.

In another preferred process of the invention, the bidentate N,N ligand L$^2$ may be added (e.g. portion wise) to a mixture of the [M(X)$_2$(L)$_3$] complex in the ketone solvent and, after stirring for a suitable period of time and at a suitable temperature, the phosphorus ligand L$^1$ may be added (e.g. portion wise). If desired, the bidentate N,N ligand L$^2$ may be added to the reaction mixture as a solution in ketone solvent. The reaction may then be stirred for a further suitable period of time and at a suitable temperature. If desired, the ketone solvent may be saturated with an inert gas (e.g. nitrogen) before it is added to the reaction mixture.

The phosphorus ligand L$^1$ may be present in stoichiometric or slight excess to the [M(X)$_2$(L)$_3$] complex. When stoichiometric quantities are utilised, the methodology does not require the use of excess ligand and thereby makes the whole process highly efficient and atom-economical for commercial production. When a slight excess is utilised, the ratio of the phosphorus ligand L$^1$:the [M (X)$_2$ (L)$_3$] complex may be about 1.05-about 1.2:about 1, such as about 1.05: about 1, about 1.1:about 1, about 1.15:about 1 or about 1.2:about 1.

The bidentate N,N ligand L$^2$ may be present in stoichiometric or slight excess to the [M(X)$_2$(L)$_3$] complex. When stoichiometric quantities are utilised, the methodology does not require the use of excess ligand and thereby makes the whole process highly efficient and atom-economical for commercial production. When a slight excess is utilised, the ratio of the bidentate N,N ligand L$^2$:the [M(X)$_2$(L)$_3$] complex may be about 1.05-1.2:about 1, such as about 1.05: about 1, about 1.1:about 1, about 1.15:about 1 or about 1.2:about 1.

The reaction may be carried out under an inert atmosphere, such as under nitrogen or argon, preferably nitrogen.

The process of the invention may be preferably carried out at one or more temperatures in the range of about −10° C. to the reflex temperature of the ketone solvent e.g. about 120° C. More preferably, the process of the invention may be carried out from about −5° C. to about 80° C., such as about 00° C. to about 50° C., for example 15° C. to about 30° C., for instance, room temperature. It is preferred that the temperature is maintained below the decomposition temperature, and so, when the [M(X)$_2$(L)$_3$] starting material and/or the [M(X)$_2$(L$^1$)$_m$(L$^2$)] product are known to decompose within the temperature ranges given above, the temperature should be maintained below the decomposition temperature.

The reaction may be carried out for a period of from about several minutes to about 72 hours but is usually complete within about 24 hours. On completion, the [M(X)$_2$(L$^1$)$_m$ (L$^2$)] product is separated from the reaction mixture by any appropriate method which is dependent upon the physical form of the product. Generally, when the [M(X)$_2$(L$^1$)$_m$(L$^2$)] complex is a solid, it may be recovered from the reaction mixture by filtering, decanting or centrifuging. If desired, the reaction mixture may be allowed to cool to a temperature which is above room temperature and below the reaction temperature of the ketone solvent (for example, about 45-50° C. when the ketone solvent is methyl ethyl ketone) before recovering the [M(X)$_2$(L$^1$)$_m$(L$^2$)] complex. Recovering the [M(X)$_2$(L$^1$)$_m$(L$^2$)] complex while the reaction mixture remains warm has the advantage that the free phosphorus ligand L$^1$ and/or its oxide (if present) is more soluble in warm ketone solvent, thus facilitating the separation of the [M(X)$_2$(L$^1$)$_m$ (L$^2$)] complex from the reaction mixture. If free phosphorus ligand L$^1$ and/or its oxide is present, the presence of these compounds may colour the [M(X)$_2$(L$^1$)$_m$ (L$^2$)] product. In this case, the [M(X)$_2$(L$^1$)$_m$(L$^2$)] complex may be stirred one or more times (e.g. 1, 2 or 3 times) in ketone solvent (e.g. acetone) until the free phosphorus ligand L$^1$ and/or its oxide is substantially removed. Alternatively or in addition, the [M(X)$_2$(L$^1$)$_m$(L$^2$)] complex may be washed one or more times (e.g. 1, 2 or 3 times) with ketone solvent. The ketone solvent aliquots may be warmed (e.g. to 45-50° C.) before the [M(X)$_2$(L$^1$)$_m$(L$^2$)] complex is washed. The [M(X)$_2$(L$^1$)$_m$(L$^2$)] complex may then be dried using known methods, for example at temperatures in the range 10-60° C. and preferably 20-40° C. under 1-30 mbar vacuum for 1 hour to 5 days. If desired the complex may be recrystallized, although this is generally not necessary.

Alternatively, the ketone solvent may be removed (for example, by distillation or stripping methods) from the solution of the [M(X)$_2$(L$^1$)$_m$(L$^2$)] product until a more concentrated solution of the [M(X)$_2$(L$^1$)$_m$(L$^2$)] product in a remaining portion of the ketone solvent is obtained. Then, an anti-solvent selected from low boiling alcohols or alkanes may be added to cause precipitation of the complex.

Suitable alcohols have boiling points below 160° C. and more preferably below 120° C. Examples of alcohol solvents included but are not limited to methanol, ethanol, propanol isomers (e.g. n-propanol or iso-propanol), butanol isomers (e.g. n-butanol, isobutanol or tert-butanol), pentanol isomers (e.g. 1-propanol, 2-pentanol, 3-pentanol, neopentyl alcohol, tert-pentyl alcohol, iso-pentyl alcohol or cyclopropanol) and hexanol isomers (e.g. 1-hexanol, 2-hexanol, 3-hexanol or cyclohexanol). Preferred examples are methanol, ethanol, n-propanol, isopropanol, n-butanol, isobutanol or tert-butanol. A particularly preferred alcohol solvent is isopropanol. Suitable alkanes have boiling points at atmospheric pressure between 0 to 150° C. Alkanes that may be used are low boiling alkanes such as pentane isomers, hexane isomers, heptane isomers or octane isomers. Preferably, the alkane is n-pentane, n-hexane cyclohexane or n-heptane and more preferably cyclohexane. The [M(X)$_2$ (L$^1$)$_m$ (L$^2$)] complex may then be dried using known methods, for example at temperatures in the range 10-60° C. and preferably 20-40° C. under 1-30 mbar vacuum for 1 hour to 5 days. If desired the complex may be recrystallized, although this may not be necessary.

The [M(X)$_2$(L$^1$)$_m$(L$^2$)] complex may be prepared on a large scale and, in this respect, the inventors have carried out the present process on a scale of up to 2 kg.

The [M(X)$_2$(L$^1$)$_m$(L$^2$)] complex obtained may contain residual ketone solvent. Hence, the complexes thus obtained may be suitable as catalysts for applications using ketone solvents.

The [M(X)$_2$(L$^1$)$_m$(L$^2$)] complex prepared according to the process of the present invention is substantially trans-[M (X)$_2$ (L$^1$)$_m$(L$^2$)] i.e. the [M(X)$_2$(L$^1$)$_m$(L$^2$)] complex comprises the structure:

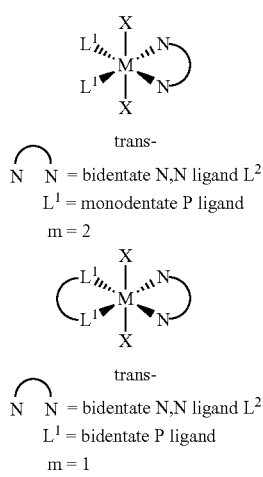

The trans- terminology is determined with reference to orientation of the anionic ligands. In this respect, the octahedral complex is described as trans- when the anionic ligands are 180° C. to each other. Conversely, the octahedral complex is described as cis- when the anionic ligands are mutually adjacent to each other.

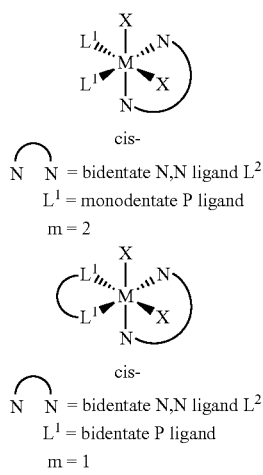

In one embodiment, the [M(X)$_2$(L$^1$)$_m$(L$^2$)] complex may be selected from the group consisting of:
trans-[RuCl$_2$ (dppp) AMPY];
trans-[RuCl$_2$ (dppb) AMPY];
trans-[RuCl$_2$ (dppf) AMPY];
trans-[RuCl$_2$ (DCyPFc) AMPY]; and
trans-[RuCl$_2$ (Josiphos*) AMPY].

In another aspect, the present invention provides a process for the preparation of an [M(X)$_2$(L)$_2$(L$^2$)] complex, the process comprising the step of:

reacting an [M(X)$_2$(L)$_3$] complex with a bidentate N,N ligand L$^2$ in a ketone solvent to form the [M(X)$_2$(L)$_2$(L$^2$)] complex;

wherein,
M is ruthenium or osmium;
X is an anionic ligand;
L is a monodentate phosphorus ligand; and
L$^2$ is a bidentate N,N ligand comprising a nitrogen-containing heteroaryl group and an amino group.

M, X, L, L$^2$, the [M(X)$_2$(L)$_3$] complex, the [M(X)$_2$(L)$_2$(L$^2$)] complex, the ketone solvent, the reaction conditions and the recovery of the [M(X)$_2$(L)$_2$(L$^2$)] complex are as generally described above.

In yet another aspect, the present invention provides a process for preparing an [M(X)$_2$L(L$_1$)$_m$] complex, the process comprising the step of:

reacting an [M(X)$_2$(L)$_3$] complex with a phosphorus ligand L$^1$ in a ketone solvent to form the [M(X)$_2$[M(X)$_2$L(L$_1$)$_m$] complex;

wherein,
M is ruthenium or osmium;
X is an anionic ligand;
L is a monodentate phosphorus ligand;
L$^1$ is a monodentate phosphorus ligand which is different to L, or a bidentate phosphorus ligand;
m is 1 or 2, wherein,
when m is 1, L$^1$ is a bidentate phosphorus ligand; and
when m is 2, each L$^1$ is a monodentate phosphorus ligand.

M, X, L, L$^1$, m, the [M(X)$_2$(L)$_3$] complex, the [M(X)$_2$L (L$^1$)$_m$ complex, the ketone solvent, the reaction conditions and the recovery of the [M(X)$_2$L(L$_1$)$_m$] complex are as generally described above.

The phosphorus ligand L$^1$ also preferably includes PPh$_3$, dppf (1,1'-bis(diphenylphosphino)ferrocene), dppp (1,3-bis (diphenylphosphino)propane), dppb (1,4-bis(diphenylphosphino)butane), Dipfc (1,1'-bis(di-isopropylphosphino)ferrocene), dCyPfc (1,1'-bis(di-cyclohexylphosphino)ferrocene), Xantphos (4,5-bis(diphenylphosphino)-9,9-dimethylxanthene) and DPEPhos (bis[(2-diphenylphosphino)phenyl] ether). In one embodiment, the phosphorus ligand L$^1$ is unsubstituted. In another embodiment, the ligand L$^1$ is substituted.

In another aspect, the present invention provides a process for preparing a cis-[M(X)$_2$(L$^1$)$_m$(L$^2$)] complex, the process comprising the steps of:

a) treating a trans-[M(X)$_2$(L$^1$)$_m$(L$^2$)] complex in an alcohol solvent; and
b) heating the reaction mixture to form the cis-[M(X)$_2$(L$^1$)$_m$ (L$^2$)] complex;

wherein,
M is ruthenium or osmium;
X is an anionic ligand;
L$^1$ is a monodentate phosphorus ligand or a bidentate phosphorus ligand;
m is 1 or 2, wherein,
when m is 1, L$^1$ is a bidentate phosphorus ligand;
when m is 2, each L$^1$ is a monodentate phosphorus ligand; and
L$^2$ is a bidentate N,N ligand comprising a nitrogen-containing heteroaryl group and an amino group.

The advantage in preparing the cis-[M(X)$_2$(L$^1$)$_m$(L$^2$)] complex is that in some embodiments it may be more catalytically active in catalytic applications.

M, X, L$^1$, m, L$^2$ and the [M(X)$_2$(L$^1$)$_m$(L$^2$)] complex are as generally described above.

The trans-[M(X)$_2$(L$^1$)$_m$(L$^2$)] complex is treated in an alcohol solvent. The trans-[M(X)$_2$(L$^1$)$_m$(L$^2$)] complex may form a solution with the alcohol solvent or may form a slurry. "Slurry" means a heterogeneous mixture of at least a portion of the complex (or complexes) in the alcohol solvent. "Slurry" therefore includes a mixture of a complex or complexes which are partially present as a solid, as well as being partially dissolved in the alcohol solvent. The complexes which can be slurried include the trans-[M(X)$_2$(L$^1$)$_m$(L$^2$)] starting material, and/or the cis-[M(X)$_2$(L$^1$)$_m$(L$^2$)] product.

By "alcohol solvent" we mean a liquid alcohol that has a boiling point at atmospheric pressure (i.e. $1.0135 \times 10^5$ Pa) below 160° C. and more preferably below 120° C. Examples of alcohol solvents included but are not limited to methanol, ethanol, propanol isomers (e.g. n-propanol or iso-propanol), butanol isomers (e.g. n-butanol, isobutanol or tert-butanol), pentanol isomers (e.g. 1-propanol, 2-pentanol, 3-pentanol, neopentyl alcohol, tert-pentyl alcohol, iso-pentyl alcohol or cyclopropanol) and hexanol isomers (e.g. 1-hexanol, 2-hexanol, 3-hexanol or cyclohexanol). Preferred examples are methanol, ethanol, n-propanol, isopropanol, n-butanol, isobutanol or tert-butanol. A particularly preferred alcohol solvent is isopropanol. While a mixture of alcohol solvents may be used, typically a single alcohol is suitable. Preferably, the alcohol solvent is dry.

Any suitable volume of alcohol solvent may be used. For example, the ratio of alcohol solvent to trans-[M(X)$_2$(L$^1$)$_m$(L$^2$)] complex may be about 3-about 25 mL/g, such as about 4-about 20 mL/g.

The trans-[M(X)$_2$(L$^1$)$_m$(L$^2$)] complex may contain residual ketone solvent. In this case it may be desirable to first partially strip (e.g. by distillation) a portion of the alcohol solvent in order to remove remaining ketone. If desired, an additional portion of alcohol solvent may be added to the reaction mixture in order to make up the volume removed by stripping.

The reaction mixture is heated to form the cis-[M(X)$_2$(L$^1$)$_m$(L$^2$)] complex. In one embodiment, the reaction mixture may be heated to reflux. The conversion of the trans-complex to the cis-complex may be monitored by NMR.

Step (a) may further comprise a phosphorus ligand L$^1$. In this respect, therefore, step (a) involves treating a trans-[M(X)$_2$(L$^1$)$_m$(L$^2$)] complex and a phosphorus ligand L$^1$ in an alcohol solvent. The trans-[M(X)$_2$(L$^1$)$_m$(L$^2$)] complex may comprise an [M(X)$_2$(L)$_2$(L$^2$)] complex as a by-product. For example, the inventors have found that during the synthesis of trans-[RuCl$_2$ (dppb) (AMPY)], various amounts (e.g. 5-10%) of trans-[RuCl$_2$ (PPh$_3$)$_2$(AMPY)] may be formed deriving from the insertion of the AMPY ligand into the unreacted starting material [RuCl$_2$ (PPh$_3$)$_3$]. The advantages therefore of heating the trans-[M(X)$_2$(L$^1$)$_m$(L$^2$)] complex with the phosphorus ligand L$^1$ in an alcohol solvent are twofold. In this respect, without wishing to be bound by theory, the inventors believe that the phosphorus ligand L$^1$ converts the [M(X)$_2$(L)$_2$(L$^2$)] by-product (if present) to the [M(X)$_2$(L$^1$)$_m$(L$^2$)] complex and, secondly, the phosphorus ligand L$^1$ isomerises the trans-[M(X)$_2$(L$^1$)$_m$(L$^2$)] complex to the cis-[M(X)$_2$(L$^1$)$_m$(L$^2$)] complex. The inventors have noted that no isomerisation appears to occur when the trans-[M(X)$_2$(L$^1$)$_m$(L$^2$)] complex is heated in a ketone solvent, such as acetone.

The amount of the phosphorus ligand L$^1$ may be in the range of about 0.001 to about 0.7 mol eq of the molar quantity of the trans-[M(X)$_2$(L$^1$)$_m$(L$^2$)] complex, for example, about 0.002 to about 0.5 mol eq.

The reaction may be carried out for a period of from about several minutes to about 90 hours but is usually complete within about 24 hours. On completion, the cis-[M(X)$_2$(L$^1$)$_m$(L$^2$)] product is separated from the reaction mixture by any appropriate method which is dependent upon the physical form of the product. Generally, when the cis-[M(X)$_2$(L$^1$)$_m$(L$^2$)] complex is a solid, it may be recovered from the reaction mixture by filtering, decanting or centrifuging. If desired, the reaction mixture may be allowed to cool to a temperature which is above room temperature and below the refluxing temperature of the alcohol solvent (for example, about 50° C. when the alcohol solvent is isopropanol) before recovering the cis-[M(X)$_2$(L$^1$)$_m$(L$^2$)] complex. Recovering the cis-[M(X)$_2$(L$^1$)$_m$(L$^2$)] complex while the reaction mixture remains warm has the advantage that the free phosphorus ligand L$^1$ and/or its oxide (if present) is more soluble in warm alcohol solvent, thus facilitating the separation of the cis-[M(X)$_2$(L$^1$)$_m$(L$^2$)] complex from the reaction mixture. If free phosphorus ligand L$^1$ and/or its oxide is present, the presence of these compounds may colour the cis-[M(X)$_2$(L$^1$)$_m$(L$^2$)] product. In this case, the cis-[M(X)$_2$(L$^1$)$_m$(L$^2$)] complex may be stirred one or more times (e.g. 1, 2 or 3 times) with one of the above described ketone solvents (such as acetone) until the free phosphorus ligand L$^1$ and/or its oxide is substantially removed. Alternatively or in addition, the cis-[M(X)$_2$(L$^1$)$_m$(L$^2$)] complex may be washed one or more times (e.g. 1, 2 or 3 times) with alcohol solvent (such as isopropanol). The alcohol solvent aliquots may be warmed (e.g. to 50° C.) before the cis-[M(X)$_2$(L$^1$)$_m$(L$^2$)] complex is washed. The cis-[M(X)$_2$(L$^1$)$_m$(L$^2$)] complex may then be dried using known methods, for example at temperatures in the range 10-60° C. and preferably 20-40° C. under 1-30 mbar vacuum for 1 hour to 5 days. If desired the complex may be recrystallized, although this is generally not necessary.

Alternatively, the alcohol solvent may be removed (for example, by distillation or stripping methods) from the solution of the cis-[M(X)$_2$(L$^1$)$_m$(L$^2$)] product until a more concentrated solution of the cis-[M (X)$_2$(L$^1$)$_m$(L$^2$)] product in a remaining portion of the alcohol solvent is obtained. Then, an anti-solvent selected from low boiling alkanes may be added to cause precipitation of the complex. Suitable alkanes have boiling points at atmospheric pressure between 0 to 150° C. Alkanes that may be used are low boiling alkanes such as pentane isomers, hexane isomers, heptane isomers or octane isomers. Preferably, the alkane is n-pentane, n-hexane cyclohexane or n-heptane and more preferably cyclohexane. The cis-[M(X)$_2$(L$^1$)$_m$(L$^2$)] complex may then be dried using known methods, for example at temperatures in the range 10-60° C. and preferably 20-40° C. under 1-30 mbar vacuum for 1 hour to 5 days. If desired the complex may be recrystallized, although this may not be necessary.

The cis-[M(X)$_2$(L$^1$)$_m$(L$^2$)] complex may be prepared on a large scale and, in this respect, the inventors have carried out the present process on a scale of up to 1.9 kg.

In another aspect, the present invention provides a process for the preparation of a cis-[M(X)$_2$(L$^1$)$_m$ (L$^2$)] complex, the process comprising the step of:
reacting an [M(X)$_2$(L)$_2$(L$^2$)] complex with a phosphorus ligand L$^1$ in an alcohol solvent to form the cis-[M(X)$_2$(L$^1$)$_m$(L$^2$)] complex;
wherein,
M is ruthenium or osmium;
X is an anionic ligand;
L is a monodentate phosphorus ligand;
L$^1$ is a monodentate phosphorus ligand which is different to L, or a bidentate phosphorus ligand;
m is 1 or 2, wherein, when m is 1, $L^1$ is a bidentate phosphorus ligand;
when m is 2, each $L^1$ is a monodentate phosphorus ligand; and $L^2$ is a bidentate N,N ligand comprising a nitrogen-containing heteroaryl group and an amino group.

M, X, L, $L^1$, m, $L^2$, the [M(X)$_2$(L)$_2$($L^2$)] complex, the cis-[M(X)$_2$($L^1$)$_m$($L^2$)] complex, the alcohol solvent, the reaction conditions and the recovery of the cis-[M(X)$_2$($L^1$)$_m$($L^2$)] complex are as generally described above.

The cis-[M(X)$_2$($L^1$)$_m$($L^2$)] complex may be prepared in a combined process i.e. by firstly preparing the trans-[M(X)$_2$($L^1$)$_m$($L^2$)] or [M(X)$_2$(L)$_2$($L^2$)] complexes using a ketone solvent and secondly by preparing the cis-[M(X)$_2$($L^1$)$_m$($L^2$)] complex using an alcohol solvent. The advantage in doing so is that pure cis-[M(X)$_2$($L^1$)$_m$($L^2$)] complex may be obtained. This is because the process utilising the ketone solvent facilitates the removal of free phosphorus ligand thus producing a better quality trans-[M(X)$_2$($L^1$)$_m$($L^2$)] or [M(X)$_2$(L)$_2$($L^2$)] product and the process utilising the alcohol solvent facilitates the exchange of one phosphorus ligand for another (if desired) and facilitates the isomerisation of a trans-complex to the cis-complex. These advantages are lost in methods using e.g. toluene where the trans-complex and its subsequent isomerisation occur in a one-pot process.

The complexes obtained by the methods of the present invention are pure and, if desired, may be used in catalytic applications as obtained. The complexes may contain small amounts of a residual alcohol. The catalysts can be used in catalytic applications as obtained or further dried. We have found that alcohols are easier to remove than aromatic solvents such as toluene upon drying under vacuum. Furthermore the complexes obtained using the present methods are easy to filter and therefore are suited to large-scale manufacture.

In another aspect, the present invention provides a [M(X)$_2$(L) ($L^2$)] complex, wherein:
M is ruthenium or osmium;
X is an anionic ligand;
$L^1$ is a bidentate phosphorus ligand selected from the group consisting of:
(i) a ligand of formula (Ia) or (Ib):

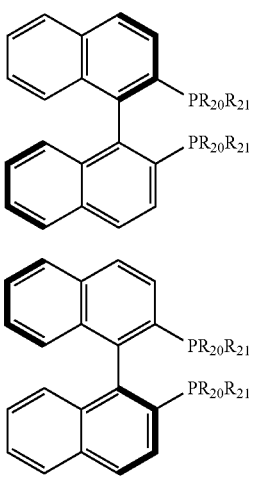

wherein,
$R_{20}$ and $R_{21}$ are each independently selected from the group consisting of unsubstituted $C_{3-20}$-cycloalkyl, substituted $C_{3-20}$-cycloalkyl, unsubstituted $C_{5-20}$-aryl and substituted $C_{5-20}$-aryl;
(ii) a ligand of formula (IIa) or (IIb):

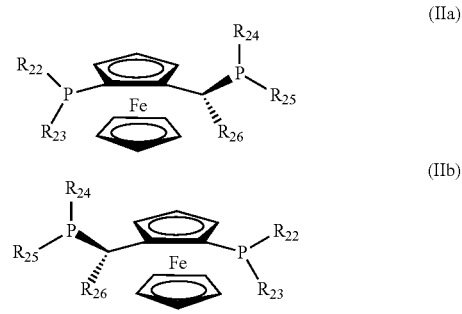

wherein,
$R_{22}$ and $R_{23}$ are independently selected from the group consisting of unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl;
$R_{24}$ and $R_{25}$ are independently selected from the group consisting of unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl; and
$R_{26}$ is selected from the group consisting of unsubstituted $C_{1-20}$-alkyl and substituted $C_{1-20}$-alkyl;
(iii) a ligand of selected from the group consisting of 1,1'-bis(di-isopropylphosphino)ferrocene, 1,1'-bis(dicyclohexylphosphino)ferrocene and 1,1'-bis(di-tert-butylphosphino)ferrocene.

and $L^2$ is a bidentate N,N ligand selected from the group consisting of ligands (1), (2) and (3):

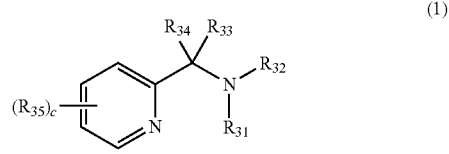

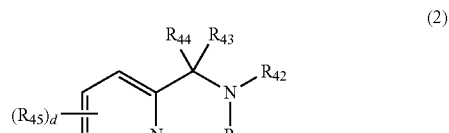

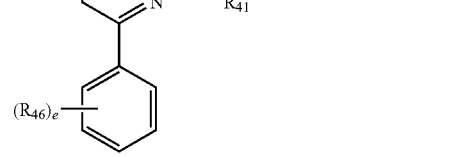

-continued (3)

wherein:
R$_{31}$ and R$_{32}$, R$_{41}$ and R$_{42}$, and R$_{51}$ and R$_{52}$ are independently selected from the group consisting of —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl and substituted C$_{4-20}$-heteroaryl;

R$_{33}$ and R$_{34}$, R$_{43}$ and R$_{44}$, and R$_{53}$ and R$_{54}$ are independently selected from the group consisting of —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl and substituted C$_{4-20}$-heteroaryl;

R$_{35}$, R$_{45}$, R$_{46}$, R$_{55}$, R$_{56}$ and R$_{57}$ are independently selected from the group consisting of —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl and substituted C$_{4-20}$-heteroaryl;

c is 0, 1, 2, 3 or 4;
d is 0, 1, 2 or 3;
e is 0, 1, 2, 3, 4 or 5;
f is 0, 1 or 2;
g is 0, 1 or 2;
h is 0, 1, 2, 3 or 4.

M, X, the ligands of formulae (Ia), (Ib), (IIa), (IIb), 1,1'-bis(di-isopropylphosphino)ferrocene, 1,1'-bis(di-cyclohexylphosphino)ferrocene, 1,1'-bis(di-tert-butylphosphino)ferrocene and L$^2$ are as generally described above.

The [M(X)$_2$(L$^1$)(L$^2$)] complex may be a trans-[M(X)$_2$(L$^1$)(L$^2$)] complex or a cis-[M(X)$_2$(L$^1$)(L$^2$)] complex.

The complex may be selected from the group consisting of:
[RuCl$_2$ (1,1'-bis(di-cyclohexylphosphino)ferrocene) (2-(aminomethyl)pyridine)];
[RuCl$_2$ (1,1'-bis(di-isopropylphosphino)ferrocene) (2-(aminomethyl)pyridine)];
[RuCl$_2$ (1,1'-bis(di-tert-butylphosphino)ferrocene) (2-(aminomethyl)pyridine)];
[RuCl$_2$ (1-[2-diphenylphosphinoferrocenyl]ethyldiphenylphosphine) (2-(aminomethyl)pyridine)]; and
[RuCl$_2$ (TolBINAP) (2-(aminomethyl)pyridine)].

The invention will be further illustrated by reference to the following non-limiting examples.

EXAMPLES

All Examples were carried out under inert conditions using high purity nitrogen.

Solvents and the 2-(aminomethyl)pyridine reagent are commercial grade. RuCl$_2$(PPh$_3$)$_3$ used in the Examples is commercially available as Ru-100 from Johnson Matthey Catalysis and Chiral Technologies. Unless otherwise specified, CDCl$_3$ was used for NMR analysis. An NMR assay was obtained immediately after or shortly after the preparation of the sample.

Abbreviations
AMPY 2-(aminomethyl)pyridine
DCyPFc 1,1'-bis(dicyclohexylphosphino)ferrocene
DPEPhos bis[(2-diphenylphosphino)phenyl]ether
dppp 1,3-bis(diphenylphosphino)propane
dppb 1,4-bis(diphenylphospino)butane
dppf 1,1'-bis(diphenylphosphino)ferrocene
eq. equivalent
IPA isopropanol
L Litre
MEK methyl ethyl ketone
mL milliliter
RT Room Temperature
Xantphos 4,5-bis(diphenylphosphino)-9,9-dimethylxanthene Example 1

Preparation of trans-RuCl$_2$(dppb)(AMPY)

In a 1 L round bottom flask were introduced, under nitrogen atmosphere, RuCl$_2$(PPh$_3$)$_3$ (100.0 g) and acetone (600 mL). The mixture was stirred at RT and dppb (1.1 eq) was added portion wise (10.0 g each). After stirring at RT for 3 hours, AMPY (1.0 eq) was added and the reaction mixture was stirred overnight at RT. After 18 hours the precipitate was filtered and dried in vacuum (yellow solid). The title product was analysed by $^{31}$P NMR (CDCl$_3$, RT).

Preparation of cis-RuCl(dppb)(AMPY)

In a 1 L round bottom flask were introduced, under nitrogen atmosphere, trans-RuC$_2$(dppb)(AMPY) (73.0 g), dppb (0.5 eq) and dry IPA (350 mL). The reaction mixture was refluxed overnight. After 15 hours the reaction mixture was cooled to RT and the precipitate was filtered. The precipitate was collected into a round bottom flask and stirred in acetone (ca 150 mL) at RT for 2 hours. The solid was filtered and dried in vacuum (yellow solid). The title product was analysed by $^{31}$P NMR (CDCl$_3$, RT).

Example 2

Preparation of trans-RuCl$_2$(PPh$_3$)$_2$(AMPY)

In a 1 L round bottom flask were introduced RuCl$_2$(PPh$_3$)$_3$ (100.0 g) and acetone (500 mL). The mixture was degassed and stirred under nitrogen atmosphere for 1 hour at RT. AMPY (1.2 eq) was added drop wise and the reaction mixture was stirred at RT overnight. The precipitate was filtered, washed with acetone and dried in vacuum (yellow solid). The title product was analysed by $^{31}$P NMR (CDCl$_3$, RT).

Preparation of cis-RuCl(dppb)(AMPY)

In a 400 mL schlenk, under nitrogen atmosphere, were refluxed trans-RuC$_2$(PPh$_3$)$_2$(AMPY) (30.0 g), dppb (1.2 eq) and dry IPA (200 mL). After 2 hours the reaction mixture was cooled to RT and stirred for 1 hour. The precipitate was filtered and dried in vacuum. The green solid was stirred in acetone for 2 hours at RT. The precipitate was filtered, but still a light green colour (due to free phosphine and its oxide) was present, so the solid was stirred again in acetone until a yellow solid was recovered and dried in vacuum. The title product was analysed by $^{31}$P NMR (CDCl$_3$, RT).

Example 3

Preparation of trans-RuCl$_2$(dppf)(AMPY)

In a 250 mL round bottom flask were introduced, under nitrogen atmosphere, RuCl$_2$(PPh$_3$)$_3$(3.155 g) and acetone (60 mL). The mixture was stirred at RT and dppf (2.0 g) was added. After stirring at RT for 3 hours, AMPY (0.34 mL) was added and the reaction mixture was stirred at RT over a weekend. The precipitate was filtered and dried in vacuum to give a yellow solid. The title product was analysed by $^{31}$P NMR (CDCl$_3$, RT).

Preparation of cis-RuCl$_2$(dpp)(AMPY)

In a 400 mL Schlenk were introduced, under nitrogen atmosphere, trans-RuCl$_2$(dppf)(AMPY) (20.0 g) and dry IPA (120 mL). The mixture was refluxed overnight. The reaction mixture was cooled to RT and the precipitate was filtered and dried in vacuum to give a yellow solid (19 g). The title product was analysed by $^{31}$P NMR (CDCl$_3$, RT).

Example 4

Preparation of trans-[(PPh$_3$)$_2$RuCl$_2$ AMPY] (AMPY/Ru-100=1.1)

Into a 2 L stirred glass reactor are introduced 300 g of RuCl$_2$(PPh$_3$)$_3$ as solid followed by 1.2 L of MEK. Stirring is started immediately and the slurry is stirred for 4 hours. In a separate reactor, 150 ml of MEK are mixed with 37.225 g of AMPY. This mixture is added over a period of 20 minutes to the RuCl$_2$(PPh$_3$)$_3$ slurry. Upon completion, the second reactor is refilled twice with 150 ml of MEK and the contents are added over periods of 10 minutes each to the main reactor. The reaction mixture is stirred for 17 hours. The obtained thick slurry is suction filtered using a Buechner funnel and filter paper until a wet cake of product is obtained. (Duration less than 25 minutes). Washing with MEK is continued until the MEK filtrate is uncoloured. The yellow product is dried at 10 mbar, 30° C. for 48 hours. Trans-[(PPh$_3$)$_2$RuCl$_2$ AMPY] (255 g) is obtained as fine powder which contains by $^1$H NMR 3% w/w MEK.

Example 5

Preparation of cis-[dppp RuCl$_2$ AMPY]

Into a 1 L stirred glass reactor equipped with an efficient reflux condenser are introduced 80.407 g trans-[(PPh$_3$)$_2$ RuCl$_2$ AMPY] (product of Example 4) and 49.495 g of dppp ligand (1.2 eq with respect to Ru). 600 mL of IPA are added and the stirred slurry is heated with an oil bath set at 107° C. This results in a refluxing of the IPA solvent. Shortly after reaching the reaction temperature the appearance of the slurried solid changes to a brighter yellow. After heating is continued for 60 hours it is switched off and the slurry is allowed to cool to 50° C. The hot slurry is suction filtered using a Buechner funnel and filter paper until a wet cake of product is obtained. This cake is further washed with 3×100 ml of IPA (solvent aliquots heated to 50° C. before use). The yellow product is dried at 10 mbar, 60° C. for 48 hours. After drying the product (70.1 g) retains 4% w/w IPA. $^1$H and $^{31}$P{$^1$H} NMR data in accordance with the literature: Organometallics 2005, 24, 1660 (compound 5).

Example 6

Preparation of trans-[dppp RuCl$_2$ AMPY]

Into a 1 L stirred glass reactor are introduced 80.407 g trans-[(PPh$_3$)$_2$RuCl$_2$ AMPY] (product of Example 4) and 49.495 g of dppp ligand (1.2 eq with respect to Ru). 600 mL of MEK are added and the stirred slurry is heated with an oil bath set at 60° C. After heating is continued for 60 hours it is switched off and the slurry is allowed to cool to 45° C. The hot slurry is suction filtered using a Buechner funnel and filter paper until a wet cake of product is obtained. This cake is further washed with 3×100 ml of MEK (solvent aliquots heated to 50° C. before use). The red coloured MEK filtrates are discarded. The yellow product (68.7 g) is dried at 10 mbar, 30° C. for 48 hours. After drying the product (68.7 g) retains MEK.

The identity of the solid is confirmed by $^1$H and $^{31}$P{$^1$H} NMR analysis to be trans-[(dppp RuCl$_2$ AMPY]: $^1$H NMR: δ 8.37 (1H, C$\underline{H}$ in 6 position of AMPY pyridine), 7.71-6.62 (23H, several multiplets, remaining pyridine and phenyl C$\underline{H}$), 4.30 (2H, broad s, C$\underline{H}_2$—N of AMPY), 2.64 and 1.85 (6H, broad multiplets, C$\underline{H}_2$ of coordinated dppp), the N$\underline{H}_2$ resonances are very broad. $^{31}$P{$^1$H}-NMR: 44.58 (d, J=49 Hz), 34.69 (d, J=49 Hz).

Example 6 demonstrates that the use of the ketone solvent MEK at 60° C. enables the dppp/PPh$_3$ ligand exchange but not the isomerisation of the trans-[dppp RuCl$_2$ AMPY] product.

Example 7

Preparation of cis-[dppp RuCl$_2$ AMPY]

Into a 1 L stirred glass reactor equipped with an efficient reflux condenser are introduced 60 g trans-[dppp RuCl$_2$ AMPY], as obtained in Example 6, and 3.00 g of dppp ligand and 600 mL of IPA are added. The stirred slurry is heated with an oil bath set at 107° C. This results in a refluxing of the IPA solvent. After heating is continued for 60 hours it is switched off and the slurry is allowed to cool to 50° C. The hot slurry is suction filtered using a Buechner funnel and filter paper until a wet cake of product is obtained. This cake is further washed with IPA (solvent aliquots heated to 50° C. before use) until the IPA filtrate is colourless. The yellow product is dried at 10 mbar, 60° C. for 48 hours. After drying the product (57.3 g) retains 4.5% w/w IPA. $^1$H and $^{31}$P{$^1$H} NMR data in accordance with that obtained in example 5.

Example 8

Preparation of cis-[dppf RuCl$_2$ AMPY]

Into a 1 L stirred glass reactor equipped with an efficient reflux condenser are introduced 80.407 g trans-[(PPh$_3$)$_2$ RuCl$_2$ AMPY] (product of Example 4) and 66.527 g of dppf ligand (1.2 eq with respect to Ru). 600 mL of IPA are added and the stirred slurry is heated with an oil bath set at 107° C. This results in a refluxing of the IPA solvent. After heating is continued for 80 hours it is switched off and the slurry is allowed to cool to 50° C. The hot slurry is suction filtered using a Buechner funnel and filter paper until a wet cake of product is obtained. This cake is further washed with 3×200 ml of IPA (solvent aliquots heated to 50° C. before use). The yellow product (85.3 g) is dried at 10 mbar, 60° C. for 48 hours. After drying the product (85.3 g) still retains 3% w/w IPA. $^1$H and $^{31}$P{$^1$H} NMR data in accordance with the literature: Chemistry—A European Journal, 2011, 17, 3474 (compound 9).

Example 9

Preparation of trans-[dppf RuCl$_2$ AMPY]

Into a 1 L stirred glass reactor are introduced 100 g of RuCl$_2$(PPh$_3$)$_3$ and 63.6 g of dppf as solids followed by 0.5 L of acetone. Stirring is started immediately and the slurry is stirred for 18 hours. 11.280 g of AMPY are added after dilution in 100 ml of acetone over the period of one hour, followed by 100 ml of acetone to keep the product slurry stirring efficiently. The reaction mixture is stirred for 24 hours. The obtained thick slurry is suction filtered using a Buechner funnel and filter paper until a wet cake of product is obtained. Washing with acetone is continued until the acetone filtrate is uncoloured. The yellow product is dried at 10 mbar, 30° C. for 48 hours. Trans-[dppf RuCl$_2$ AMPY] (84 g) is obtained as fine powder which contains by $^1$H NMR 4% w/w acetone. $^1$H and $^{31}$P{$^1$H} NMR data in accordance with the literature: Chemistry—A European Journal, 2011, 17, 3474 (compound 8).

Example 10

Preparation of cis-[dppf RuC$_2$ AMPY]

Into a 1 L stirred glass reactor equipped with an efficient reflux condenser is introduced 40 g of trans-[(dppf RuCl$_2$ AMPY] (product of Example 9). 800 mL of IPA is added and the stirred slurry is heated with an oil bath set at 107° C. This results in a refluxing of the IPA solvent. After heating is continued for 20 hours it is switched off and the slurry is allowed to cool to 50° C. The hot slurry is suction filtered using a Buechner funnel and filter paper until a wet cake of product is obtained. This cake is further washed with 3×200 ml of IPA (solvent aliquots heated to 50° C. before use). The yellow product is dried at 10 mbar, 60° C. for 48 hours. After drying the product (39.4 g) retains 2% w/w IPA. 1H and $^{31}$P{H} NMR data in accordance with cis-[(dppf RuCl$_2$ AMPY] as obtained in Example 8.

Example 11

Preparation of trans-[dppb RuCl$_2$ AMPY]

Into a 20 L stirred glass reactor are introduced 1000 g of RuCl$_2$(PPh$_3$)$_3$ and 490 g of dppb as solids followed by 13 L of acetone. Stirring is started immediately and the slurry is stirred for 4 hours. In a separate reactor, 1 L of acetone is mixed with 124.03 g of AMPY. This mixture is added over a period of 30 minutes to the slurry in the 20 L reactor. Upon completion, the second reactor is refilled twice with 0.5 L of acetone and the contents are added over periods of 10 minutes each to the main reactor. The reaction mixture is stirred for 16 hours. The obtained thick slurry is suction filtered using a Buechner funnel and filter paper (Whatman 541) until a wet cake of product is obtained. This requires 120 minutes to process. Washing with acetone is continued until the acetone filtrate is uncoloured. The yellow product is dried at 10 mbar, 30° C. for 48 hours. Trans-[dppb RuCl$_2$ AMPY] (648 g) is obtained as fine powder which contains by $^1$H NMR 4% w/w acetone. $^1$H and $^{31}$P{$^1$H} NMR data in accordance with the literature: Organometallics 2005, 24, 1660 (compound 2).

Example 12

Large scale preparation of trans-[dppb RuCl$_2$ AMPY]

Into a 20 L stirred glass reactor are introduced 2000 g of RuCl$_2$(PPh$_3$)$_3$ and 980 g of dppb as solids followed by 13 L of MEK. Stirring is started immediately and the slurry is stirred for 4 hours. In a separate reactor, 1 L of MEK is mixed with 248.1 g of AMPY. This mixture is added over a period of 30 minutes to the slurry in the 20 L reactor. Upon completion, the second reactor is refilled twice with 0.5 L of MEK and the contents are added over periods of 10 minutes each to the main reactor. The reaction mixture is stirred for 16 hours. The obtained thick slurry is suction filtered using a Buechner funnel and filter paper (Whatman 541) until a wet cake of product is obtained. This requires 10 minutes to process. Washing with MEK is continued until the MEK filtrate is uncoloured. The yellow product is dried at 10 mbar, 30° C. for 48 hours. Trans-[dppb RuCl$_2$ AMPY] (1320 g) is obtained as fine powder which contains by $^1$H NMR 5% w/w MEK.

The identity of the solid is confirmed by $^1$H and $^{31}$P{$^1$H} NMR analysis to the same as obtained in Example 11.

Example 13 (Comparative)

Large scale preparation of [dppb RuCl$_2$ AMPY] using toluene as reaction solvent Into a 20 L stirred glass reactor are introduced 2000 g of RuCl$_2$(PPh$_3$)$_3$ and 980 g of dppb as solids followed by 13 L of toluene. Stirring is started immediately and the slurry is stirred for 4 hours. In a separate reactor, 1 L of toluene is mixed with 248.1 g of AMPY. This mixture is added over a period of 30 minutes to the slurry in the 20 L reactor. Upon completion, the second reactor is refilled twice with 0.5 L of toluene and the contents are added over periods of 10 minutes each to the main reactor. The reaction mixture is stirred for 16 hours. The obtained thick slurry is suction filtered using a Buechner funnel and filter paper (Whatman 541) until a wet cake of product is obtained. This requires 510 minutes to process. Washing with toluene is done only once to cope with the excessive time required to filter. The filter cake obtained is of a large volume and retains by weight 50% of toluene compared to less than 10% in Examples 11 or 12. The filter cake is dried at 10 mbar, 30° C. for 120 hours and the product (1375 g) is obtained as one dried out solid lump. It is broken up to a very fine solid by grinding with mortar and pestle and is identified by $^1$H and $^{31}$P{$^1$H} NMR analysis as a 9/1 mixture of trans- and cis-[dppb RuCl$_2$ AMPY].

On comparing the present experiment with Example 12, it can be seen that the use of toluene (instead of a ketone solvent) has a number of disadvantages, for example, the filtration time is significantly longer, the product requires drying at a higher temperature for a longer time, the form of the product after drying is more difficult to handle and requires additional processing in order to produce a fine powder and the cis-isomer is present in trans-product. The process, therefore, is not suitable for large scale manufacturing.

Example 14

Large scale preparation of cis-[dppb RuCl$_2$ AMPY]

Into a stirred glass reactor equipped with an efficient reflux condenser is introduced 1900 g of trans-[dppb RuCl$_2$ AMPY] (product made using acetone as reaction solvent) and 1.9 g of dppb. 10 L of IPA is added and the stirred slurry is heated with an oil bath set at 107° C. This results in a refluxing of the IPA solvent. After heating is continued for 3 hours it is switched off and the slurry is allowed to cool to 50° C. The hot slurry is suction filtered using a Buechner funnel and filter paper until a wet cake of product is obtained. This cake is further washed with 2×5 L of IPA. The product is dried at 10 mbar, 60° C. for 48 hours. After drying the product (1790 g) retains 4% w/w IPA. $^1$H and $^{31}$P{$^1$H} NMR data in accordance with the literature: Organometallics 2005, 24, 1660 (compound 7).

Example 15

Large scale preparation of [dppb RuCl$_2$ AMPY]

Into a 20 L stirred glass reactor are introduced 2000 g of RuCl$_2$(PPh$_3$)$_3$ and 980 g of dppb as solids followed by 13 L of MEK. Stirring is started immediately and the slurry is stirred for 4 hours. In a separate reactor, 1 L of MEK is mixed with 236.8 g of AMPY. This mixture is added over a period of 30 minutes to the slurry in the 20 L reactor. Upon completion, the second reactor is refilled twice with 0.5 L of MEK and the contents are added over periods of 10 minutes each to the main reactor. The reaction mixture is stirred for 16 hours. The obtained thick slurry is suction filtered using a Buechner funnel and filter paper (Whatman 541) until a wet cake of product is obtained. This requires 10 minutes to process. Washing with MEK is continued until the MEK filtrate is uncoloured. The yellow product is dried at 10 mbar, 30° C. for 48 hours. Trans-[dppb RuCl$_2$ AMPY] (1320 g) is obtained as fine powder which contains by $^1$H NMR 3% w/w MEK.

Example 16

Preparation of cis-[dppb RuCl$_2$ AMPY]

Into a stirred glass reactor with a unit attached that allows both distillation and solvent reflux is introduced 42.81 g of trans-[(dppb RuCl$_2$ AMPY] and 0.105 g of dppb. 530 mL of IPA is added and the stirred slurry is heated with an oil bath set at 112° C. This results in distillation of the IPA solvent which is commenced until 100 ml of solvent is collected. Then the unit is switched to solvent reflux and the oil bath is set at 107° C. After heating is continued for 36 hours it is switched off and the slurry is allowed to cool to 50° C. The slurry at 50° C. is suction filtered using a Buechner funnel and filter paper until a wet cake of product is obtained. This cake is further washed with 2×100 mL of IPA. The product is dried at 10 mbar, 60° C. for 48 hours. After drying the product (42.7 g) still retains 5% w/w IPA.

Example 17

Preparation of cis-[dppb RuCl$_2$ AMPY]

30 g of trans-[dppb RuCl$_2$ AMPY] (prepared using acetone as reaction solvent), 2 g of dppb and 200 ml of IPA are heated to reflux for 3 hours. The obtained slurry is filtered and washed with small quantities of IPA. The product is analysed by $^{31}$P{$^1$H} NMR and is shown to be composed of cis-[dppb RuCl$_2$ AMPY] (less than 2% remaining trans isomer). $^1$H and $^{31}$P{$^1$H} NMR data in accordance with the literature: Organometallics 2005, 24, 1660 (compound 7).

Example 18 (Comparative)

Preparation of cis-[dppb RuCl$_2$ AMPY]

30 g of trans-[dppb RuCl$_2$ AMPY], 2 g of dppb and 200 ml of toluene are heated to reflux for 5 hours. The obtained slurry is filtered. The product is analysed by $^{31}$P{$^1$H} NMR and is shown to be composed of only 20% cis-[dppb RuCl$_2$ AMPY] and 80% trans-[dppb RuCl$_2$ AMPY]. The filtrate and the filter cake are recombined and heated to reflux for further 15 hours to complete the isomerisation.

On comparing Examples 17 and 18, it can be seen that the isomerisation of trans-[dppb RuCl$_2$ AMPY] to cis-[dppb RuCl$_2$ AMPY] in isopropanol occurs in a shorter time (3 hours compared to 20 hours) and at a lower temperature as the boiling point of isopropanol is 82° C. compared to 110-111° C. for toluene.

Example 19

Preparation of [DPEPhos RuCl$_2$PPh$_3$]

Into a 400 mL stirred glass reactor are introduced 25.9 g of RuCl$_2$(PPh$_3$)$_3$ and 16.0 g of DPEPhos as solids followed by 300 mL of MEK. Stirring is started immediately and the slurry is stirred for 18 hours. The resulting yellow orange slurry is filtered using a Buechner funnel and filter paper until a wet cake of product is obtained. Washing with MEK is continued until the MEK filtrate is uncoloured. The yellow product is dried at 10 mbar, 30° C. for 48 hours. It is obtained as fine powder which contains by $^1$H NMR 0.2% w/w MEK in near quantitative yield. The solid is analysed by 1H and $^{31}$P{$^1$H} NMR analysis.

Example 20

Preparation of [XantPhos RuCl$_2$PPh$_3$]

Into a 400 mL stirred glass reactor are introduced 24.0 g of RuCl$_2$(PPh$_3$)$_3$ and 16.0 g of XantPhos as solids followed by 300 mL of MEK. Stirring is started immediately and the slurry is stirred for 18 hours. The resulting yellow orange slurry is filtered using a Buechner funnel and filter paper until a wet cake of product is obtained. Washing with MEK is continued until the MEK filtrate is uncoloured. The orange yellow product is dried at 10 mbar, 30° C. for 48 hours. It is obtained as fine powder which contains by $^1$H NMR 0.4% w/w MEK in near quantitative yield. The solid is analysed by $^1$H and $^{31}$P{$^1$H} NMR analysis.

Example 21

Preparation of [DCyPFc RuCl$_2$ AMPY]

Into a 200 mL stirred glass reactor are introduced 3.2 g of RuCl$_2$(PPh$_3$)$_3$ and 2.32 g of DCyPFc as solids followed by 100 mL of nitrogen saturated MEK. Stirring is started immediately and the slurry is stirred for 28 hours. $^{31}$P{$^1$H} NMR analysis of a NMR sample obtained by diluting a sample from the reaction mixture with C$_6$D$_6$ shows that all DCyPFc has reacted and that the only free phosphine is PPh$_3$ released from RuCl$_2$(PPh$_3$)$_3$.

To the intermediate slurried in MEK is added 0.42 g of AMPY after dilution in 10 ml of MEK over the period of 10 minutes. The reaction mixture is stirred for 60 hours. The obtained thick slurry of a tan brown product is suction filtered using a Buechner funnel and filter paper until a wet cake of product is obtained. Washing with MEK is continued until the MEK filtrate is uncoloured. The yellow product is dried at 10 mbar, 30° C. for 48 hours. A sample was slurried in IPA and again filtered.

The identity of the solid is confirmed by a combination of $^1$H and $^{31}$P{$^1$H} NMR analysis. By $^{31}$P{$^1$H}NMR analysis 2 isomers with δ=51 ppm (major broad resonance) and δ=48 ppm (minor broad resonance) are visible. The AMPY resonances for the major complex are δ=9.94 (d), 7.73 (t), 7.40 (t), 7.35 (t) (all integration as 0.75H) 5.07 (s, 1.5H), the AMPY resonances for the minor complex are δ=9.80 (d), 8.06 (t), 7.93 (t), 7.64 (t) (all integration as 0.25H), 5.01 (s, 0.5H). The 2×4 C<u>H</u> resonances of ferrocene are at δ=4.23 (m), 4.08 (m). The remaining resonances of the cyclohexyl-resonances (44) are a broad series of multiplets at δ=2.2-0.94 ppm.

Example 22

Preparation of [Josiphos* RuCl$_2$ AMPY]

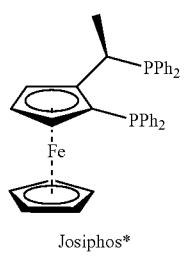

Josiphos*

Into a 400 mL stirred glass reactor are introduced 10 g of RuCl$_2$(PPh$_3$)$_3$ and 6.8 g of Josiphos* as solids followed by 250 mL of nitrogen saturated MEK. Stirring is started immediately and the slurry is stirred and heated by an oil bath kept at 75° C. for 18 hours. After cooling to room temperature a clear solution with some orange looking fluffy precipitate is obtained. $^{31}$P{$^1$H} NMR analysis of a sample from the reaction mixture with CDCl$_3$ shows that mostly free PPh$_3$ released from RuCl$_2$(PPh$_3$)$_3$ is present with little remaining Josiphos* (which was used in excess). The [Josiphos* RuCl$_2$] intermediates (mixture of isomers) are seen as an characteristic pattern of doublet resonances: δ=69.95 (d), 67.0 (d), 65.35 (d), 60.9 (d), 55.05 (d), 52.8 (d), 43.9 (d), 32.8 (d), 8.6 (d), 6.4 (d) in the $^{31}$P{$^1$H} NMR analysis.

To the intermediate slurried in MEK is added 1.28 g of of AMPY after dilution in 100 ml of MEK over the period of 30 minutes. The reaction mixture is stirred for 35 hours and appears to give an orange brown precipitate. Upon filtration over a glass sintered filter nothing is retained on the sinter. The filtered solution is stripped partially to 30 ml of a solution which is treated with 300 ml of cyclohexane yielding yellow brown crystals of product containing only 10% w/w PPh$_3$ by $^1$H NMR and $^{31}$P{$^1$H} NMR analysis (4 g). $^{31}$P{$^1$H} NMR analysis shows that isomers of [Josiphos* RuCl$_2$ AMPY] have been formed and that the conversion of [Josiphos* RuCl$_2$] intermediates with AMPY was complete. The analysis of the stripped filtrates shows them to contain larger quantities of free phosphine (as expected from a mother liquor) and the same isomeric mixture of [Josiphos* RuCl$_2$ AMPY]. $^{31}$P{$^1$H}NMR analysis: δ=72.29 (d), 37.98 (d) major isomer 1; 60.53 (d), 43.23 (d) isomer 2; 51.09 (d), 43.75 (d) isomer 3; 70.64 (d), 35.81 (d) isomer 4; 71.17 (d), 53.11 (d) isomer 5; 57.76 (d), 46.94 (d) isomer 6 and others.

A one gram sample of the solid [Josiphos* RuCl$_2$ AMPY] is heated in IPA (1 g in 15 ml of IPA) to an oil bath temperature of 102° C. for 15 hours. The reaction forms a clear red solution which is filtered and then stripped and the residue dried for 2 hours at 50° C., 10 mbar. A major isomer of [Josiphos* RuCl$_2$ AMPY] which is very insoluble even in chlorinated solvents is obtained by 1H and $^{31}$P{$^1$H} NMR analysis. $^{31}$P{$^1$H} NMR analysis: δ=72.29 (d), 37.98 (d) major isomer 1; 60.53 (d), 43.23 (d) isomer 2; ratio of isomers 9/1.

The invention claimed is:

1. A process for preparing an [M(X)$_2$(L$^1$)$_m$(L$^2$)] complex, the process comprising the step of:
   reacting an [M(X)$_2$(L)$_3$] complex with a phosphorus ligand L$^1$ and a bidentate N,N ligand L$^2$ in a ketone solvent to form the [M(X)$_2$(L$^1$)$_m$(L$^2$)] complex;
   wherein,
   M is ruthenium or osmium;
   X is an anionic ligand;
   L is a monodentate phosphorus ligand;
   L$^1$ is an achiral bidentate phosphorus ligand;
   m is 1; and
   L$^2$ is a bidentate N,N ligand of formula (1) comprising a nitrogen-containing heteroaryl group and an amino group:

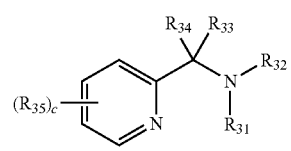

(1)

wherein:
R$_{31}$ and R$_{32}$ are, independently, —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl, or substituted C$_{4-20}$-heteroaryl;

R$_{33}$ and R$_{34}$ are, independently, —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl, or substituted C$_{4-20}$-heteroaryl;

R$_{35}$ is, independently, —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl, or substituted C$_{4-20}$-heteroaryl; and c is 0, 1, 2, 3 or 4.

2. A process for preparing a cis-[M(X)$_2$(L$^1$)$_m$(L$^2$)] complex, the process comprising the steps of:
a) treating a trans-[M(X)$_2$(L$^1$)$_m$(L$^2$)] complex in an alcohol solvent, or a mixture of an alcohol solvent and an aromatic solvent; and
b) heating the reaction mixture to form the cis-[M(X)$_2$(L$^1$)$_m$(L$^2$)] complex;
wherein,
M is ruthenium or osmium;
X is an anionic ligand;
L$^1$ is an achiral bidentate phosphorus ligand;
m is 1; and
L$^2$ is a bidentate N,N ligand of formula (1) comprising a nitrogen-containing heteroaryl group and an amino group:

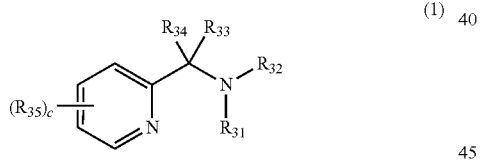

(1)

wherein:
R$_{31}$ and R$_{32}$ are, independently, —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl, or substituted C$_{4-20}$-heteroaryl;

R$_{33}$ and R$_{34}$ are, independently, —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl, or substituted C$_{4-20}$-heteroaryl;

R$_{35}$ is, independently, —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl, or substituted C$_{4-20}$-heteroaryl; and c is 0, 1, 2, 3 or 4.

3. A process according to claim 2, wherein step (a) further comprises a phosphorus ligand L$^1$.

4. A process for preparing a cis-[M(X)$_2$(L$^1$)$_m$(L$^2$)] complex, the process comprising the step of:
reacting an [M(X)$_2$(L)$_2$(L$^2$)] complex with a phosphorus ligand L$^1$ in an alcohol solvent, or a mixture of an alcohol solvent and an aromatic solvent to form the cis-[M(X)$_2$(L$^1$)$_m$(L$^2$)] complex;
wherein,
M is ruthenium or osmium;
X is an anionic ligand;
L is a monodentate phosphorus ligand;
L$^1$ is an achiral bidentate phosphorus ligand;
m is 1; and
L$^2$ is a bidentate N,N ligand of formula (1) comprising a nitrogen-containing heteroaryl group and an amino group:

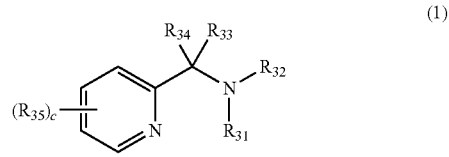

(1)

wherein:
R$_{31}$ and R$_{32}$ are, independently, —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl, or substituted C$_{4-20}$-heteroaryl;

R$_{33}$ and R$_{34}$ are, Independently —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl, or substituted C$_{4-20}$-heteroaryl;

R$_{35}$ is, independently, —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl or substituted C$_{4-20}$-heteroaryl; and c is 0, 1, 2, 3 or 4.

5. A process according to claim 1, wherein M is ruthenium.

6. A process according to claim 1, wherein L is a tertiary phosphine ligand $PR_1R_2R_3$, wherein $R_1$, $R_2$ and $R_3$ are, independently, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl, or substituted $C_{4-20}$-heteroaryl.

7. A process according to claim 1, wherein $L^1$ is an achiral, bidentate phosphorus ligand and the phosphorus atom of the phosphorus ligand is covalently bonded to either 3 carbon atoms or to n heteroatoms and 3-n carbon atoms, where n=1, 2 or 3.

8. A process according to claim 7, wherein the heteroatom is N or O.

9. A process according to claim 7, wherein the phosphorus ligand $L^1$ is dppf (1,1'-bis(diphenylphosphino)ferrocene), dppp (1,3-bis(diphenylphosphino)propane), dppb (1,4-bis(diphenylphosphino)butane), Dipfc (1,1'-bis(di-isopropylphosphino)ferrocene), or dCyPfc.

10. A process according to claim 1, wherein X is a halide.

11. A process according to claim 1, wherein the ketone solvent is acetone, methyl-ethyl ketone (MEK), methyl-isobutyl ketone (MIBK), or diethylketone.

12. A process according to claim 11, wherein the ketone solvent is acetone or methyl-ethyl ketone.

13. A process according to claim 2, wherein the alcohol solvent is methanol, ethanol, n-propanol, isopropanol, n-butanol, isobutanoL or tert-butanol.

14. A process according to claim 13, wherein the alcohol solvent is isopropanol.

* * * * *